United States Patent
Iino et al.

(10) Patent No.: US 7,459,585 B2
(45) Date of Patent: Dec. 2, 2008

(54) BENZENE DERIVATIVES AND PHARMACEUTICAL USE THEREOF

(75) Inventors: Yukio Iino, Kawasaki (JP); Kohichi Fujita, Kawasaki (JP); Takashi Tsuji, Kawasaki (JP); Ariko Kodaira, Kawasaki (JP); Kenji Takehana, Kawasaki (JP); Tsuyoshi Kobayashi, Kawasaki (JP); Takashi Yamamoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/087,531

(22) Filed: Mar. 24, 2005

(65) Prior Publication Data

US 2005/0165114 A1 Jul. 28, 2005

Related U.S. Application Data

(60) Continuation of application No. 10/387,395, filed on Mar. 14, 2003, now abandoned, which is a division of application No. 09/803,107, filed on Mar. 12, 2001, now Pat. No. 6,703,379, which is a continuation of application No. PCT/JP99/04986, filed on Sep. 13, 1999.

(30) Foreign Application Priority Data

Sep. 11, 1998 (JP) .................... 10-257804

(51) Int. Cl.
| | |
|---|---|
| C07C 233/60 | (2006.01) |
| C07C 233/61 | (2006.01) |
| C07C 233/62 | (2006.01) |
| C07C 233/63 | (2006.01) |
| C07C 309/66 | (2006.01) |
| C07C 311/21 | (2006.01) |
| C07D 209/38 | (2006.01) |
| C07D 209/48 | (2006.01) |
| C07D 211/78 | (2006.01) |

(52) U.S. Cl. .................. 564/158; 564/86; 564/153; 564/154; 564/155; 564/156; 564/157; 564/190; 562/433; 560/251; 558/50; 558/404; 548/476; 548/513; 546/323; 514/354; 514/415; 514/421; 514/423; 514/517; 514/535; 514/544; 514/563; 514/603; 514/616; 514/624

(58) Field of Classification Search .......... None
See application file for complete search history.

(56) References Cited

U.S. PATENT DOCUMENTS 4,181,519 A  1/1980  Pilgram et al.

FOREIGN PATENT DOCUMENTS

| EP | 0 767 167 | 4/1997 |
|---|---|---|
| GB | 1 255 161 | 12/1971 |
| JP | 03-014835 | 1/1991 |
| JP | 10-182551 | 7/1998 |
| WO | WO 96/35782 | 11/1996 |
| WO | WO 99/61013 | 2/1999 |

OTHER PUBLICATIONS

Database Caplus on STN, Acc. No. 1995:543429, Kitagawa et al., JP 06271762 (Sep. 27, 2004) (abstract).*
Database Caplus on STN, Acc. No. 1991:450484, Nakazawa et al., JP 03014835 (Jan. 23, 1991) (abstract).*
Database Caplus on STN, Acc. No. 1996:124039, Nakajima et al., JP 07316385 (Dec. 5, 1995) (abstract).*
V. A. Bren, et al., "Biphotochromic Norbornadiene Systems", Molecular Crystals and Liquid Crystals, 1997, vol. 297, pp. 247-253.
Database Caplus on STN, Acc. No. 1996: 124039, Nakajima et al., JP 07316385, abstract, 1996.
Database Caplus on STN, 1969:491119, Janiak, DE 1803084, Jun. 19, 1969 (abstract).
Database Caplus on STN, Acc. No. 1996:128395, Nakajima, JP 07316348 (Dec. 5, 1995) (abstract).

* cited by examiner

*Primary Examiner*—Brian J Davis
(74) *Attorney, Agent, or Firm*—Oblon, Spivak, McClelland, Maier & Neustadt, P.C.

(57) ABSTRACT

The present invention provides an AP-1 activation inhibitor, NF-kappa B activation inhibitor, inflammatory cytokine production inhibitor, matrix metalloprotease production inhibitor, inflammatory cell adhesion molecule expression inhibitor, anti-inflammatory agent, antirheumatic agent, immunosuppressant, cancer metastasis inhibitor, remedy for arteriosclerosis and antiviral agent which contain the benzene derivative of the following general formula (I) or a pharmaceutically acceptable salt thereof as an active ingredient.

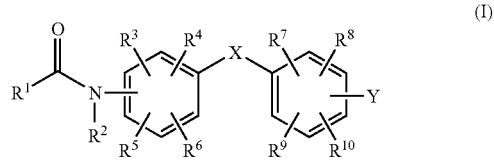

21 Claims, No Drawings

BENZENE DERIVATIVES AND PHARMACEUTICAL USE THEREOF

CROSS-REFERENCE TO RELATED APPLICATIONS

The present application is a continuation of U.S. application Ser. No. 10/387,395, filed on Mar. 14, 2003, which is a divisional of U.S. application Ser. No. 09/803,107, filed on Mar. 12, 2001, which is a continuation of International Application PCT/JP99/04986, filed on Sep. 13, 1999, which claims priority to Japanese patent application JP 10-257804, filed on Sep. 11, 1998.

BACKGROUND OF THE INVENTION

The present invention relates to benzene derivatives useful for the treatment of various inflammatory diseases and pharmaceutical compositions containing them.

It is known that various inflammatory diseases, rheumatoid diseases, immunoreactive diseases, cancer metastasis and viral diseases are caused by the abnormal production of inflammatory cytokines and matrix metalloprotease and also by the increase in the expression of inflammatory cell adhesion molecules.

Although various medicines for these diseases were developed in the prior art, further development of a medicine having a stronger efficiency, higher safety and weaker side effects is demanded.

The pathophysiological states of various chronic inflammatory diseases are considered to be caused by the continuous production of inflammation mediators such as cytokines [particularly, inflammatory cytokines including IL-1, IL-2, IL-6, IL-8 and tumor necrotizing factor (TNF)], adhesion molecules, tissue destroying enzymes (such as matrix metalloprotease), etc. by the continuous extracellular stimulation.

The inflammatory mediators are produced because the gene expression is activated by the extracellular stimulation. A substance having the most important role in this step is a transcription factor known as AP-1 or NF-kappa B. Namely, it is expected that when the activation of AP-1/NF-kappa B can be inhibited, the development of inflammation and the advance thereof into chronic stage can be prevented and that such a method will be a hopeful treatment of inflammatory diseases such as rheumatoid arthritis and various autoimmune diseases (V. C. Foletta et al., [Journal of Leukocyte Biology, 63, 139-152, 1998], P. J. Barnes et al., [The new England Journal of Medicine, 336, 1066-1071, 1997] and M. J. Suto et al., [Current Pharmaceutical Design, 3, 515-528, 1997]).

Glucocorticoid hormone (GC) which strongly inhibits the activation of intracellular AP-1 and NF-kappa B has been used as a powerful anti-inflammatory agent and immunosuppressant. However, the use of GC as a medicine is limited because it has various side effects due to hormonic action thereof and it causes rebound phenomenon.

DISCLOSURE OF THE INVENTION

The object of the present invention is to provide benzene derivatives having a remarkable medicinal effect and only a slight side effect and useful for the treatment of chronic inflammatory diseases.

Another object of the present invention is to provide a pharmaceutical composition containing the benzene derivative.

The above-described and other objects of the present invention will be apparent from the following description and Examples.

After intensive investigations made for the purpose of finding compounds having a strong activity of inhibiting the activation of AP-1 and NF-kappa B and useful as a strong remedy for chronic inflammatory diseases, the inventors have found that compounds of general formula (I) which will be described below have this effect. The present invention has been completed on the basis of this finding.

Namely, the present invention relates to benzene derivatives of the following general formula (I) or pharmaceutically acceptable salts thereof:

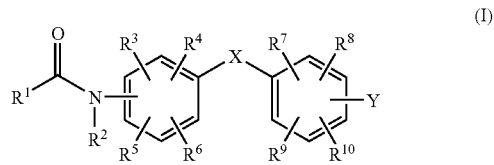

(I)

wherein $R^1$ represents a cycloalkyl group having a substituent or a cycloalkenyl group having a substituent, $R^2$ represents hydrogen atom or an alkyl group, $R^3$ to $R^{10}$, which may be the same or different from each other, represent hydrogen atom, a halogen atom, hydroxyl group, mercapto group, nitro group, cyano group, trifluoromethyl group, an alkyl group, an alkoxyl group, an alkylthio group, an amino group which may be substituted with an alkyl group or an amino-protecting group, an acyloxy group, an acyl group, carboxyl group, an alkoxycarbonyl group or carbamoyl group, —Y represents a group of following general formula (II), (III) or (IV):

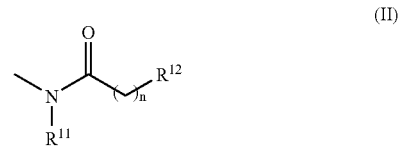

(II)

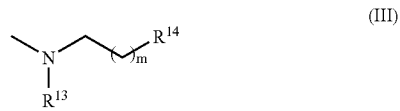

(III)

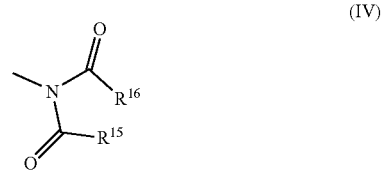

(IV)

wherein $R^{11}$ and $R^{13}$ each represent hydrogen atom or an alkyl group, $R^{12}$ and $R^{14}$ each represent an alkyl group which may have a substituent, a cycloalkyl group which may have a substituent, a cycloalkenyl group which may have a substituent, an aryl group which may have a substituent, an aromatic heterocyclic group having one or more hetero atom, which may have a substituent, or a saturated heterocyclic group having one or more hetero atoms, which may have a substituent, and $R^{15}$ and $R^{16}$ each represent an alkyl group or an aryl group which may form a ring together, and n and m each represent an integer selected from among 0 to 6, and —X— represents an interatomic bond, or any of —O—, —O—$CHR^{17}$—, —O—$CHR^{18}$—O—, —O—CO—, —CO—O—, —O—CS—, —CS—O—, —S—, —SO—, —$SO_2$—, —S—$CHR^{19}$—, —$CHR^{20}$—S—, —S—CO—, —CO—S—, —S—CS—, —CS—S—, —$SO_2$—$NR^{21}$—, —$NR^{22}$—$SO_2$—, —$NR^{23}$—, —$NR^{24}$—$CHR^{25}$—, —$CHR^{26}$—$NR^{27}$—, —CO—, —C(=$NOR^{28}$)—, —C(=$CHR^{29}$)—, —CO—$CHR^{30}$—, —$CHR^{31}$—CO—, —CO—$NR^{32}$—, —$NR^{33}$—CO—, —$CR^{34}R^{35}$—, —$CHR^{36}$—$CHR^{37}$— and —$CR^{38}$=$CR^{39}$— wherein $R^{17}$, $R^{18}$, $R^{19}$, $R^{20}$, $R^{21}$, $R^{22}$, $R^{25}$, $R^{26}$, $R^{29}$, $R^{30}$, $R^{31}$, $R^{32}$, $R^{33}$, $R^{34}$, $R^{38}$ and $R^{39}$ each represent hydrogen atom or an alkyl group, $R^{23}$, $R^{24}$, $R^{27}$ and $R^{28}$ each represent hydrogen atom, an alkyl group or an acyl group, $R^{36}$ and $R^{37}$ each represent hydrogen atom, hydroxyl group or an alkyl group, and $R^{35}$ represents hydrogen atom, hydroxyl group, mercapto group, cyano group, an alkyl group, which may have a substituent, an alkoxyl group, an alkylthio group, an acyloxy group, an amino group which may be substituted with an alkyl group or an amino-protecting group, carboxyl group, an alkoxycarbonyl group or carbamoyl group.

The present invention provides a pharmaceutical composition, particularly AP-1 and NF-kappa B activation inhibitor, inflammatory cytokine production inhibitor, matrix metalloprotease production inhibitor and inflammatory cell adhesion molecule expression inhibitor. They can be used as anti-inflammatory agent, antirheumatic agent, immunosuppressant, cancerous metastasis inhibitor, remedy for arteriosclerosis and antiviral agent, which contains the above-described benzene derivative or a pharmaceutically acceptable salt thereof as an active ingredient.

DESCRIPTION OF THE PREFERRED EMBODIMENTS

The detailed description of the present invention will be made below.

The term "halogen atoms" include fluorine atom, chlorine atom, bromine atom and iodine atom.

The term "hetero atoms" herein indicates oxygen atom, sulfur atom and nitrogen atom. Among them, nitrogen atom is preferred.

The term "cycloalkyl groups" herein indicates cyclic alkyl groups of 3 to 6 carbon atoms such as cyclopropyl group, cyclobutyl group, cyclopentyl group and cyclohexyl group. Among them, cyclopropyl group is preferred.

The term "cycloalkenyl groups" herein indicates cyclic alkenyl groups having 3 to 6 carbon atoms such as cyclopropenyl group, cyclobutenyl group, cyclopentenyl group and cyclohexenyl group.

The term "alkyl groups" herein indicates linear or branched alkyl groups having 1 to 6 carbon atoms such as methyl group, ethyl group, n-propyl group, isopropyl group, n-butyl group, isobutyl group, sec-butyl group, tert-butyl group, n-pentyl group, isopentyl group, tert-pentyl group, neopentyl group, 2-pentyl group, 3-pentyl group, n-hexyl group and 2-hexyl group. Among them, methyl group and ethyl group are preferred.

The term "alkoxyl groups" herein indicates linear or branched alkoxyl groups having 1 to 6 carbon atoms such as methoxy group, ethoxy group, n-propoxy group, isopropoxy group, n-butoxy group, isobutoxy group, sec-butoxy group and tert-butoxy group. Among them, methoxy group and ethoxy group are preferred.

The term "alkylthio groups" indicates linear or branched alkylthio groups having 1 to 6 carbon atoms such as methylthio group, ethylthio group, n-propylthio group, isopropylthio group, n-butylthio group, isobutylthio group, sec-butylthio group and tert-butylthio group.

The term "amino groups which may be substituted with an alkyl group" indicates unsubstituted amino groups or amino groups mono- or di-substituted with alkyl group(s). The alkyl groups are those listed above as examples of the "alkyl groups". "Amino groups which may be substituted with an alkyl group" are, for example, amino group, methylamino group, ethylamino group, propylamino group, isopropylamino group, dimethylamino group, diethylamino group, dipropylamino group, diisopropylamino group and methylethylamino group.

Amino-protecting groups are ordinary protecting groups which are not particularly limited so far as they are capable of protecting the amino group from reactions. They include, for example, acyl groups such as formyl group, acetyl group and pivaloyl group; and alkoxycarbonyl groups such as methoxycarbonyl group, ethoxycarbonyl group, tert-butoxycarbonyl group and fluorenyl-9-methoxycarbonyl group.

The term "acyloxy groups" indicates linear or branched acyloxy groups having 1 to 6 carbon atoms or acyloxy groups having a substituted or unsubstituted aryl group, such as formyloxy group, acetyloxy group, propionyloxy group, butyroyloxy group, isobutyroyloxy group, valeroyloxy group, isovaleroyloxy group, pivaloyloxy group, hexanoyloxy group, acryloyloxy group, methacryloyloxy group, crotonoyloxy group, isocrotonoyloxy group, benzoyloxy group and naphthoyloxy group.

The term "acyl groups" indicates linear or branched acyl groups having 1 to 6 carbon atoms or acyl groups having a substituted or unsubstituted aryl group, such as formyl group, acetyl group, propionyl group, butyroyl group, isobutyroyl group, valeroyl group, isovaleroyl group, pivaloyl group, hexanoyl group, acryloyl group, methacryloyl group, crotonoyl group, isocrotonoyl group, benzoyl group and naphthoyl group.

The term "alkoxycarbonyl groups" indicates those having a linear or branched alkyl group 1 to 6 carbon atoms, such as methoxycarbonyl group, ethoxycarbonyl group, propoxycarbonyl group, isopropoxycarbonyl group, n-butoxycarbonyl group, isobutoxycarbonyl group, sec-butoxycarbonyl group and tert-butoxycarbonyl group.

The term "carbamoyl groups" herein indicates, for example, carbamoyl group, N-methylcarbamoyl group, N-ethylcarbamoyl group, N-propylcarbamoyl group, N,N-dimethylcarbamoyl group, N,N-diethylcarbamoyl group, pyrrolidinocarbonyl group and piperidinocarbonyl group.

The term "aryl groups" herein indicates, for example, phenyl group, pentenyl group, indenyl group, naphthyl group and fluorenyl group. Among them, phenyl group is preferred.

The term "aromatic heterocyclic groups having one or more hetero atoms" herein indicates, for example, pyranyl group, pyridyl group, pyridazyl group, pyrimidyl group, pyrazyl group, furyl group, thienyl group, pyrrolyl group, oxazolyl group, isoxazolyl group, thiazolyl group, isothiazolyl group, imidazolyl group, triazolyl group, tetrazolyl group, pyrazolyl group, furazanyl group, thiadiazolyl group and indolyl group. Among them, pyridyl group, pyrimidyl group, imidazolyl group and triazolyl group are preferred. Pyridyl group is particularly preferred.

The term "saturated heterocyclic groups having one or more hetero atoms" herein indicates, for example, pyrrolidyl group, piperidyl group, piperazinyl group, morpholinyl group, tetrahydrofuryl group, tetrahydropyranyl group and tetrahydrothienyl group. 2-Pyrrolidyl group is particularly preferred.

The term "having a substituent" in the expressions "cycloalkyl groups having a substituent", "cycloalkenyl groups having a substituent" and "cyclopropyl group having a substituent" indicates that such groups are substituted with at least one substituent. The substituents may be the same or different from one another, and the position of the substituent is not particularly limited. Concretely, the substituents are, for example, halogen atoms, alkyl groups which may have a substituent, carboxyl group, alkoxycarbonyl groups, cyano group and amino group which may be substituted with an alkyl group or amino-protecting group.

The term "which may have a substituent" in the expressions "alkyl groups which may have a substituent", "cycloalkyl groups which may have a substituent" and "cycloalkenyl groups which may have a substituent" indicates that these groups may have a substituent or substituents on the alkyl chain or on the ring. The substituents may be the same or different from each other and the position of the substituent is not particularly limited. The substituents are, for example, halogen atoms, alkyl groups which may have a substituent, hydroxyl group, alkoxyl groups, carboxyl group, alkoxycarbonyl groups, cyano group and amino group which may be substituted with an alkyl group or an amino-protecting group.

The term "which may have a substituent" in the expressions "aryl groups which may have a substituent" and "aromatic heterocyclic groups having one or more hetero atoms, which may have a substituent" indicates that these groups may have 1 to 3 substituents on the ring. The substituents may be the same or different from each other and the position of the substituent is not particularly limited. The substituents are, for example, halogen atoms, alkyl groups which may have a substituent, hydroxyl group, alkoxyl groups, carboxyl group, alkoxycarbonyl groups, cyano group and amino groups which may be substituted with an alkyl group or an amino-protecting group.

The term "which may have a substituent" in the expression "saturated heterocyclic rings having one or more hetero atoms, which may have a substituent" indicates that these groups may have 1 to 10 substituents on the ring. The substituents may be the same or different from each other and the position of the substituent is not particularly limited. The substituents are, for example, halogen atoms, alkyl groups which may have a substituent, hydroxyl group, alkoxyl groups, carboxyl group, alkoxycarbonyl groups, cyano group and amino groups which may be substituted with an alkyl group or an amino-protecting group.

The expression of $R^{15}$ and $R^{16}$ reading "an alkyl group or aryl group which may form a ring together" indicates groups of, for example, following formulae (V), (VI) and (VII) when they form a ring:

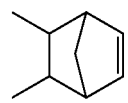

(V)

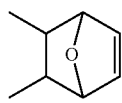

(VI)

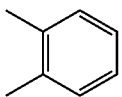

(VII)

In the benzene derivatives of the present invention, those shown by general formula (I) wherein $R^1$ represents a cycloalkyl group having a substituent and pharmaceutically acceptable salts thereof exhibit a remarkable effect. The substituents are preferably alkyl groups, more preferably lower alkyl groups having 1 to 3 carbon atoms. Particularly preferred substituents are di-lower alkyl groups and particularly dimethyl group. A remarkable effect of the compounds is obtained when $R^1$ is a cyclopropyl group having the above-described substituent, particularly 2,2-dimethylcyclopropyl group or 2,2-dichlorocyclopropyl group.

$R^2$ is preferably hydrogen atom.

$R^3$ to $R^{10}$ are each preferably hydrogen atom, a lower alkyl group or a halogen. They are each particularly preferably hydrogen atom.

Y is preferably a group of general formula (II).

$R^{11}$ and $R^{13}$ are each preferably hydrogen atom.

$R^{12}$ and $R^{14}$ are each preferably a cycloalkyl group having a substituent. The substituent is preferably an alkyl group, particularly an alkyl group having 1 to 3 carbon atoms, or a di-lower alkyl group, particularly dimethyl group. $R^{12}$ and $R^{14}$ are each more preferably a cyclopropyl group having the above-described substituent, particularly 2,2-dimethylcyclopropyl group or 2,2-dichlorocyclopropyl group.

$R^{15}$ and $R^{16}$ are each an alkyl or aryl group which may form a ring together, preferably a group of formula (V), (VI) or (VII) given above.

X is preferably —O—, —O—CHR$^{17}$—, —S—, —SO—, —SO$_2$—, —S—CHR$^{19}$—, —SO$_2$—NR$^{21}$—, —NR$^{23}$—, —CO—, —C(=NOR$^{28}$)—, —C(=CHR$^{29}$)—, —CO—NR$^{32}$—, —CR$^{34}$R$^{35}$—, —CHR$^{36}$—CHR$^{37}$— or —CR$^{38}$=CR$^{39}$— wherein $R^{17}$, $R^{19}$, $R^{23}$, $R^{28}$, $R^{29}$, $R^{34}$, $R^{36}$ and $R^{37}$ are each preferably hydrogen atom. $R^{21}$ and $R^{32}$ are each preferably hydrogen atom or a lower alkyl group. $R^{35}$ is preferably hydrogen atom, hydroxyl group, an alkyl group, which may have a substituent, an alkoxyl group, an acyloxy group, an amino group which may be substituted with an amino-protecting group or an alkoxycarbonyl group.

X is further preferably —O—, —S—, —S—CHR$^{19}$—, —NR$^{23}$—, —CR$^{34}$R$^{35}$— or —CHR$^{36}$—CHR$^{37}$—. X is particularly preferably —CR$^{34}$R$^{35}$—. $R^{19}$, $R^{23}$, $R^{34}$, $R^{35}$, $R^{36}$ and $R^{37}$ are each preferably as described above.

When $R^1$ in general formula (I) is cyclopropyl group having a substituent, it is preferred that the carbon atom adjacent to carbonyl group on cyclopropyl group has absolute configuration S. On the other hand, when $R^1$ in general formula (I) is cyclopropyl group having a substituent, it is also preferred that the carbon atom adjacent to carbonyl group on cyclopropyl group has absolute configuration R.

A remarkable effect can be obtained when both $R^1$ and $R^{12}$, in general formula (I), are 2,2-dimethylcyclopropyl group or 2,2-dichlorocyclopropyl group and n is 0, or when both $R^1$ is 2,2-dimethylcyclopropyl group or 2,2-dichlorocyclopropyl group, $R^{12}$ is an aryl group which may have a substituent and n is 1.

Benzene derivatives of following general formula (Ia) or pharmaceutically acceptable salts thereof are preferred in the compounds of general formula (I):

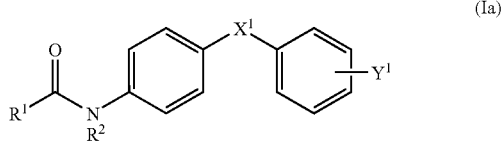

(Ia)

wherein $R^1$ and $R^2$ are defined in general formula (I),
$Y^1$ is as defined in general formulae (II) and (III),
$R^{11}$, $R^{13}$, n and m are as defined in general formulae (II) and (III),
$R^{12}$ and $R^{14}$ each represent an alkyl group which may have a substituent, a cycloalkyl group which may have a substituent, a cycloalkenyl group which may have a substituent, an aryl group which may have a substituent or an aromatic heterocyclic group having one or more hetero atoms, which may have a substituent, and
—X$^1$— represents —O—, —O—CHR$^{17}$—, —CHR$^{18}$—O—, —O—CO—, —CO—O—, —O—CS—, —CS—O—, —S—, —SO—, —SO$_2$—, —S—CHR$^{19}$—, —CHR$^{20}$—S—, —S—CO—, —CO—S—, —S—CS—, —CS—S—, —SO$_2$—NR$^{21}$—, —NR$^{22}$—SO$_2$—, —NR$^{23}$—, —NR$^{24}$—CHR$^{25}$—, —CHR$^{26}$—NR$^{27}$—, —CO—, —C(=NOR$^{28}$)—, —C(=CHR$^{29}$)—, —CO—CHR$^{30}$—, —CHR$^{31}$—CO—, —CO—NR$^{32}$—, —NR$^{33}$—CO—, —CR$^{34}$R$^{35}$—, —CHR$^{36}$—CHR$^{37}$— or —CR$^{38}$=CR$^{39}$— wherein $R^{17}$ through $R^{39}$ are as defined in formula (I).

Preferred examples of $R^1$, $R^2$, $R^{11}$, $R^{13}$, n, m, $R^{12}$, $R^{14}$ and $R^{17}$ through $R^{39}$ in general formula (Ia) are as described above with reference to formula (I).

The pharmaceutically acceptable salts are as follows: When the compounds of the present invention are completely acidic, the salts of them are, for example, ammonium salts, alkali metal salts (such as, preferably, sodium and potassium salts), alkaline earth metal salts (such as, preferably calcium and magnesium salts) and organic base salts such as dicyclohexylamine salts, benzathine salts, N-methyl-D-glucan salts, hydramine salts, and salts of amino acids such as arginine and lysine. When the compounds of the present invention are completely alkaline, the salts of them are, for example, acid-addition salts such as those with inorganic acids, for example, hydrochloric acid, sulfuric acid, nitric acid and phosphoric acid, and also those with organic acids, for example, acetic acid, lactic acid, citric acid, tartaric acid, maleic acid, fumaric acid and monomethylsulfuric acid. If necessary, the salts may be in a hydrous form of in the form of hydrates.

The compounds of the present invention may be in the form of isomers such as optical isomers and geometrical isomers, hydrates, solvated products and crystals of any form.

The compounds of the present invention can be synthesized by methods described below.

For example, compounds of the present invention represented by above general formula (I), wherein —Y is represented by formula (II), n is 0 and both ends of which are the same, can be obtained by reacting one equivalent of a corresponding diamine compound with at least two equivalents of a corresponding acid halide such as, e. g. an acid chloride, in the presence of a base or by reacting it with at least two equivalents of a carboxylic acid in the presence of a coupling reagent as shown below:

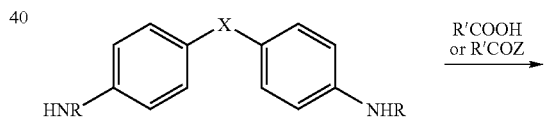

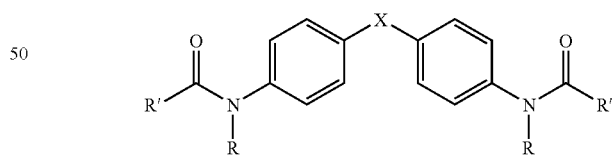

wherein X is as defined above, R represents hydrogen atom or an alkyl group, R' represents a cycloalkyl group having a substituent or a cycloalkenyl group having a substituent, and Z represents a halogen atom.

The compound wherein —X— is —CO—, obtained by the above-described reaction, can be converted into compounds of the following formulae of the present invention by, for example, a method shown in Examples given below.

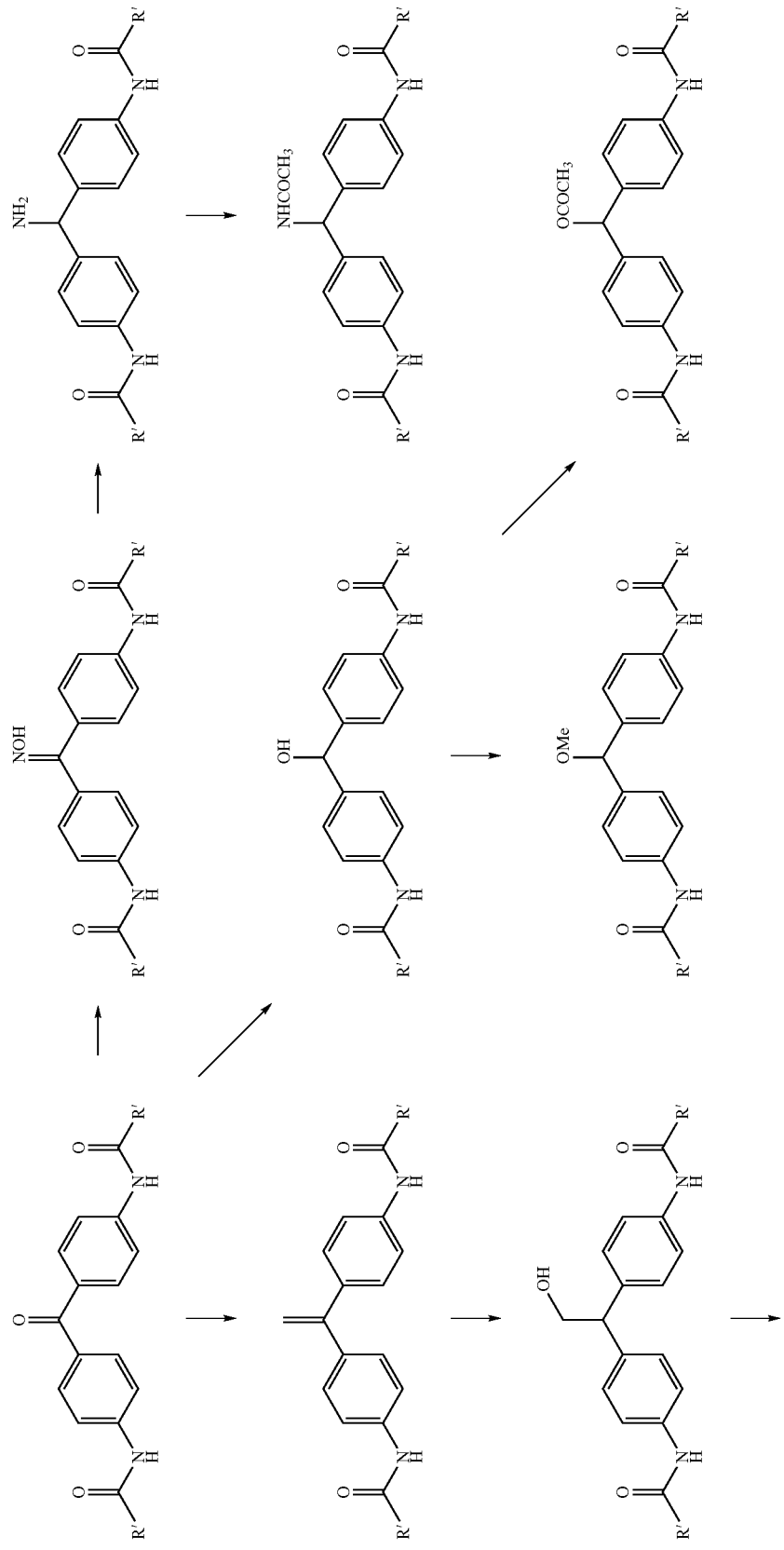

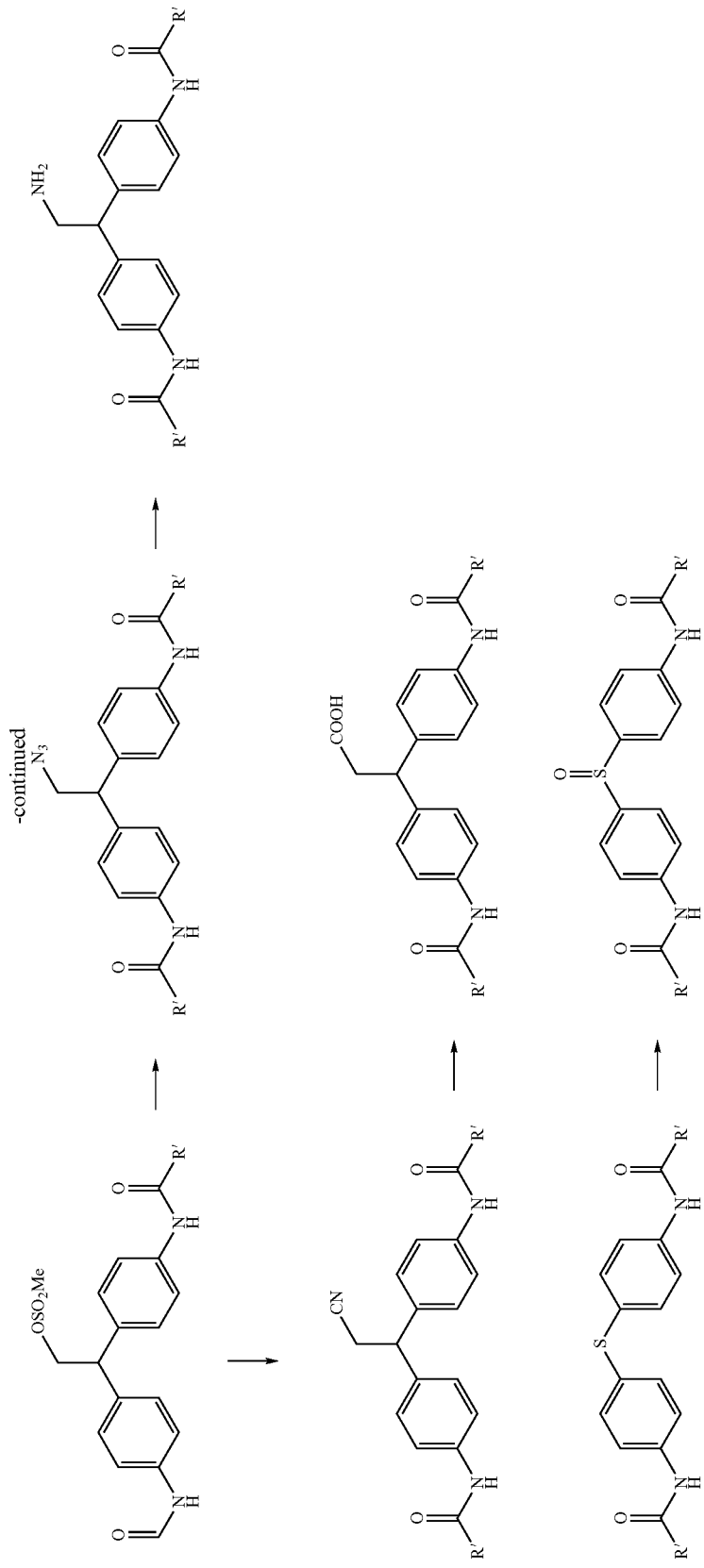

wherein R' represents a cycloalkyl group having a substituent or a cycloalkenyl group having a substituent.

Compounds of the present invention represented by above general formula (I), wherein —Y— is represented by formula (II) and both ends of which are different from each other, can be obtained by reacting one equivalent of a corresponding diamine compound with about one equivalent of a corresponding acid halide such as, e. g. an acid chloride, in the presence of a base or by reacting one equivalent of the diamine compound with about one equivalent of a carboxylic acid in the presence of a coupling reagent to introduce a substituent into an end of the diamine compound and then reacting the obtained product with an acid halide or carboxylic acid having a structure different from the acid halide or carboxylic acid used in the previous step as shown below:

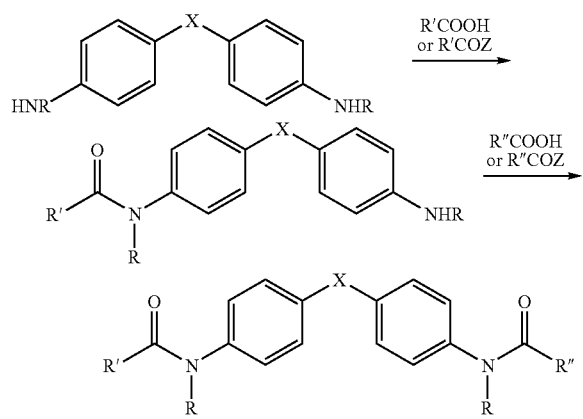

wherein X is as defined above, R represents hydrogen atom or an alkyl group, R' represents a cycloalkyl group having a substituent or a cycloalkenyl group having a substituent, R" represents an alkyl group which may have a substituent, a cycloalkyl group which may have a substituent, a cycloalkenyl group which may have a substituent, an aryl group which may have a substituent, an aromatic heterocyclic group having one or more hetero atoms, which may have a substituent, or a saturated heterocyclic ring having one or more hetero atoms, which may have a substituent, and Z represents a halogen atom.

Further, compounds of the above formula wherein —X— represents —CO—, obtained by the above-described reaction, can be converted into compounds shown in Examples given below by the above-described functional group-converting reaction.

Intended compounds of above formula (I) wherein —Y— is represented by formula (III) in the present invention can be obtained by reacting one equivalent of a corresponding diamine compound as the starting material with about one equivalent of a corresponding acid halide such as an acid chloride in the presence of a base, or by reacting one equivalent of a diamine compound with about one equivalent of a carboxylic acid in the presence of a coupling reagent to introduce a substituent into an end of the diamine compound and then reacting the obtained product with an alkyl halide which may have a substituent or with an aldehyde which may have a substituent in the presence of a reducing agent.

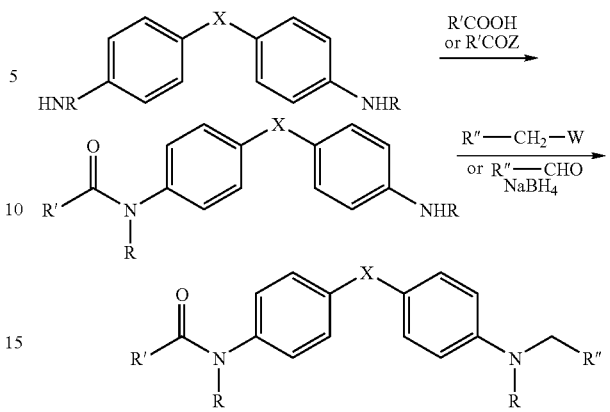

wherein X is as defined above, R represents hydrogen atom or an alkyl group, R' represents a cycloalkyl group having a substituent or a cycloalkenyl group having a substituent, R" represents an alkyl group which may have a substituent, a cycloalkyl group which may have a substituent, a cycloalkenyl group which may have a substituent, an aryl group which may have a substituent, an aromatic heterocyclic group having one or more hetero atoms, which may have a substituent, or a saturated heterocyclic group having one or more hetero atoms, which may have a substituent, and Z and W each represent a halogen atom.

The compounds of the present invention can be synthesized by applying these processes or by an ordinary process.

The compounds of the present invention obtained by the above-described processes can be purified by a purification method usually employed in the synthesis of organic compounds such as extraction, distillation, crystallization or column chromatography.

The compounds of the present invention thus obtained have an activity of inhibiting the activation of AP-1 and NF-kappa B, and they are useful for the treatment of inflammatory diseases caused by these transcription factors. Namely, these compounds inhibit gene expression of inflammatory cytokines, matrix metalloprotease and inflammatory cell adhesion molecules. They are useful as anti-inflammatory agent, anti-rheumatic agent, immunosuppressant, cancerous metastasis inhibitor and antiviral agent without side effects such as hormonal effects.

When the compounds of the present invention are used as anti-inflammatory agents, they can given by oral, intravenous or percutaneous administration or by eye dropping method. The dosage, which varies depending on the symptoms and age of the patient and also administration method, is usually 1 to 3,000 mg/kg/day.

Preparations containing the compounds of the present invention can be prepared by an ordinary method. The preparations may be in the form of an injection, tablets, granules, grains, powders, capsules, cream or suppositories. Carriers used for producing the preparations are, for example, lactose, glucose, D-mannitol, starch, crystalline cellulose, calcium carbonate, kaolin, starch, gelatin, hydroxypropylcellulose, hydroxypropylmethylcellulose, polyvinylpyrrolidone, ethanol, carboxymethylcellulose, calcium salt of carboxymethylcellulose, magnesium stearate, talc, acetylcellulose, sucrose, titanium oxide, benzoic acid, para-hydroxybenzoic esters, sodium dehydroacetate, gum arabic, tragacanth, methylcellulose, egg yolk, surfactants, simple syrup, citric acid, distilled water, ethanol, glycerol, propylene glycol, macrogol, sodium monohydrogenphosphate, sodium dihydrogenphosphate, sodium phosphate, glucose, sodium chloride, phenol, thimerosal, p-hydroxybenzoic esters and sodium hydrogensulfite. They are suitably selected depending on the form of the preparation, and mixed with the compounds of the present invention.

The amount of the active ingredient of the present invention in the preparation of the present invention is not particularly limited because it varies in a wide range depending on the form of the preparation. However, the amount is usually 0.01 to 100% by weight, and preferably 1 to 100% by weight, based on the whole composition.

EXAMPLES

The following Examples will further illustrate the present invention, which by no means limit the invention.

Compounds synthesized in Examples 1 to 55 are as follows:

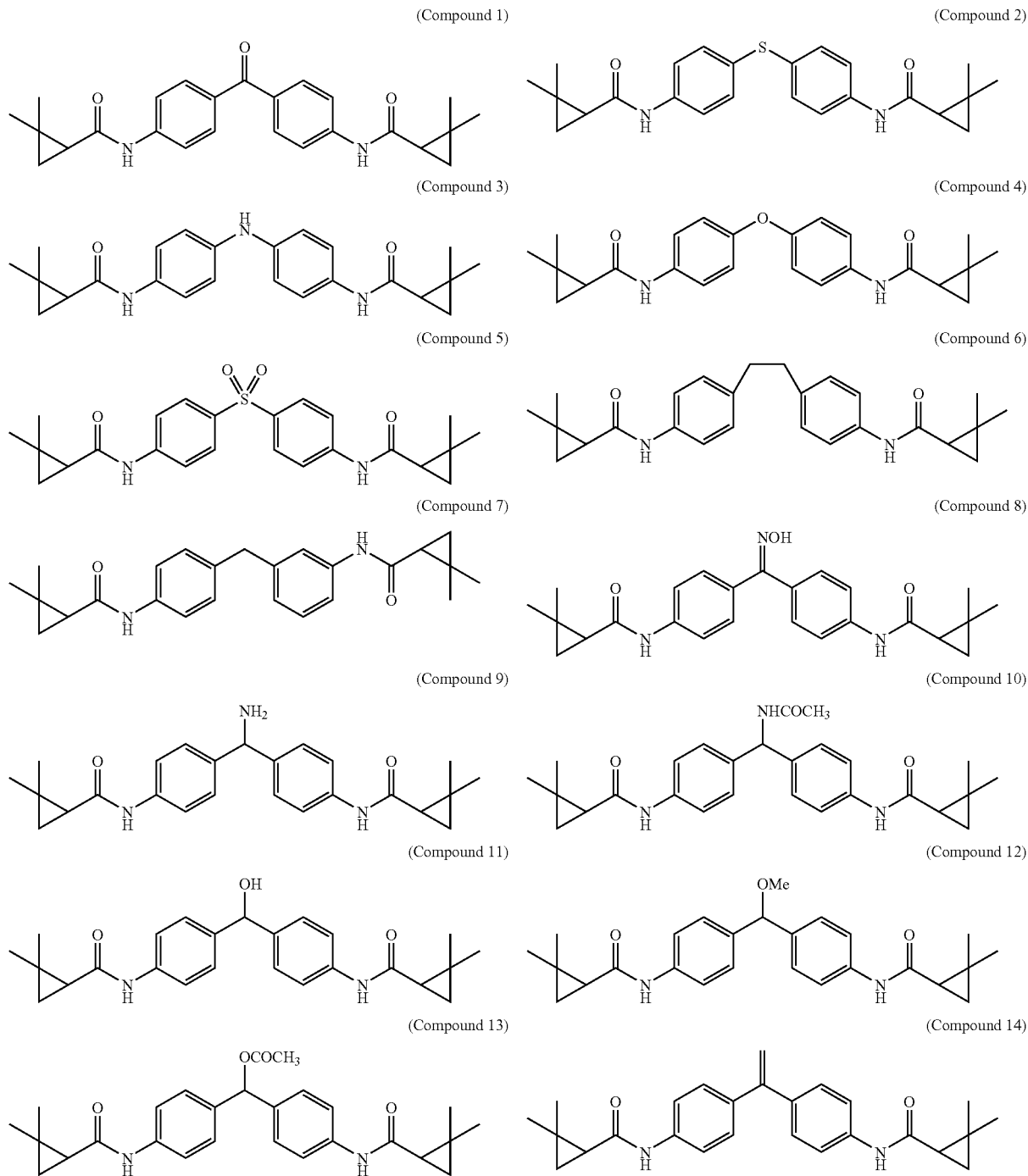

-continued
(Compound 15)
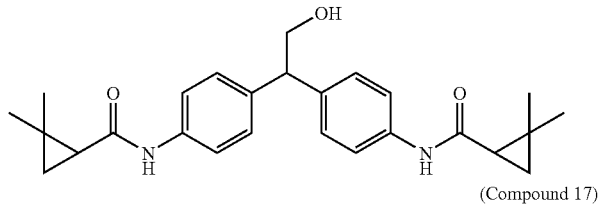
(Compound 16)
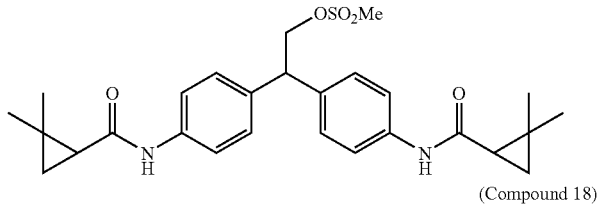
(Compound 17)
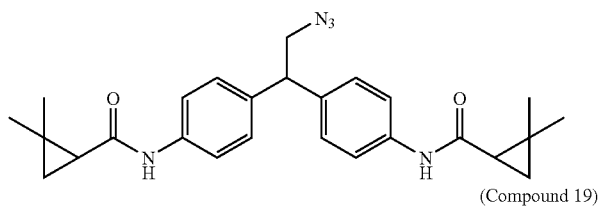
(Compound 18)
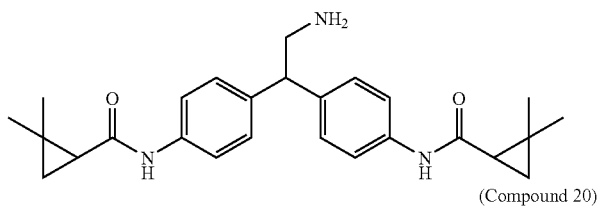
(Compound 19)
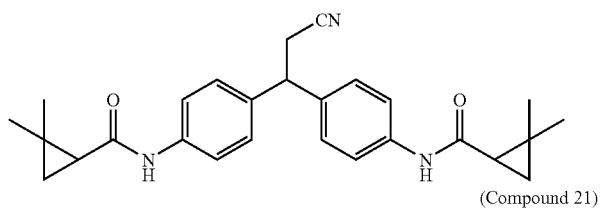
(Compound 20)
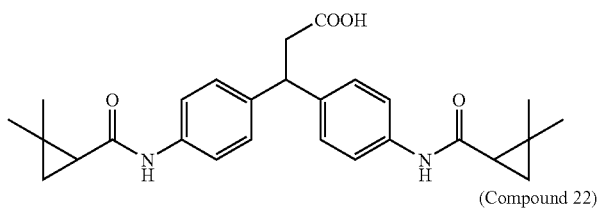
(Compound 21)
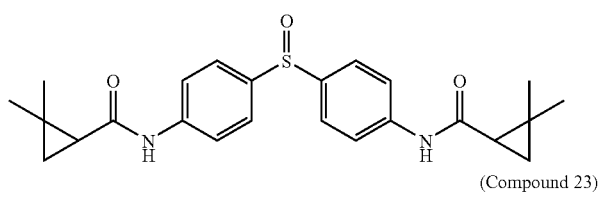
(Compound 22)
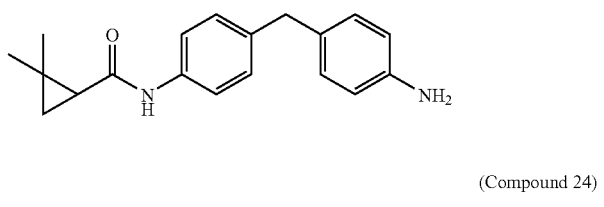
(Compound 23)
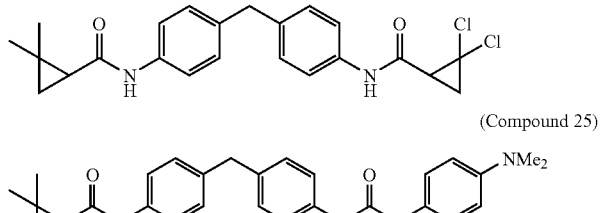
(Compound 24)
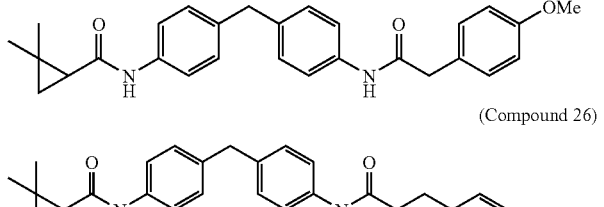
(Compound 25)
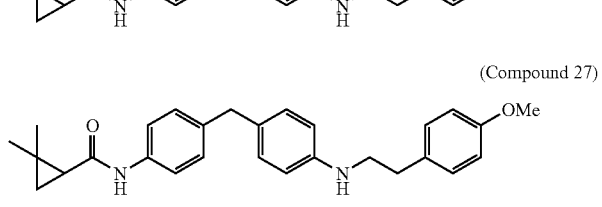
(Compound 26)
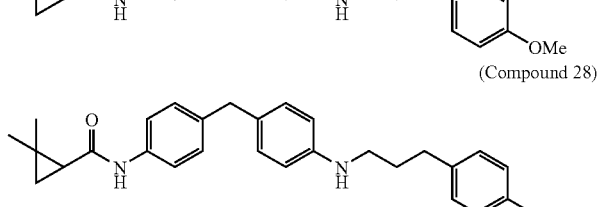
(Compound 27)
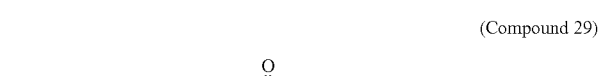
(Compound 28)
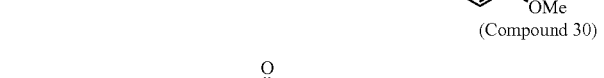
(Compound 29)
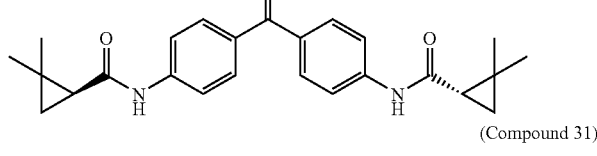
(Compound 30)
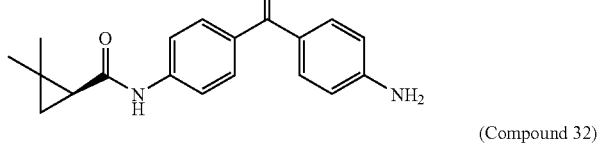
(Compound 31)
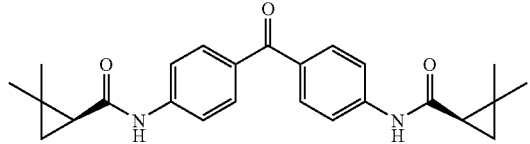
(Compound 32)
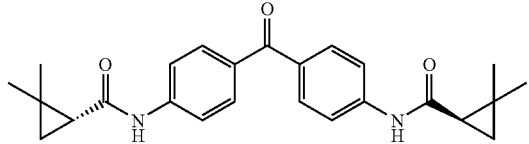

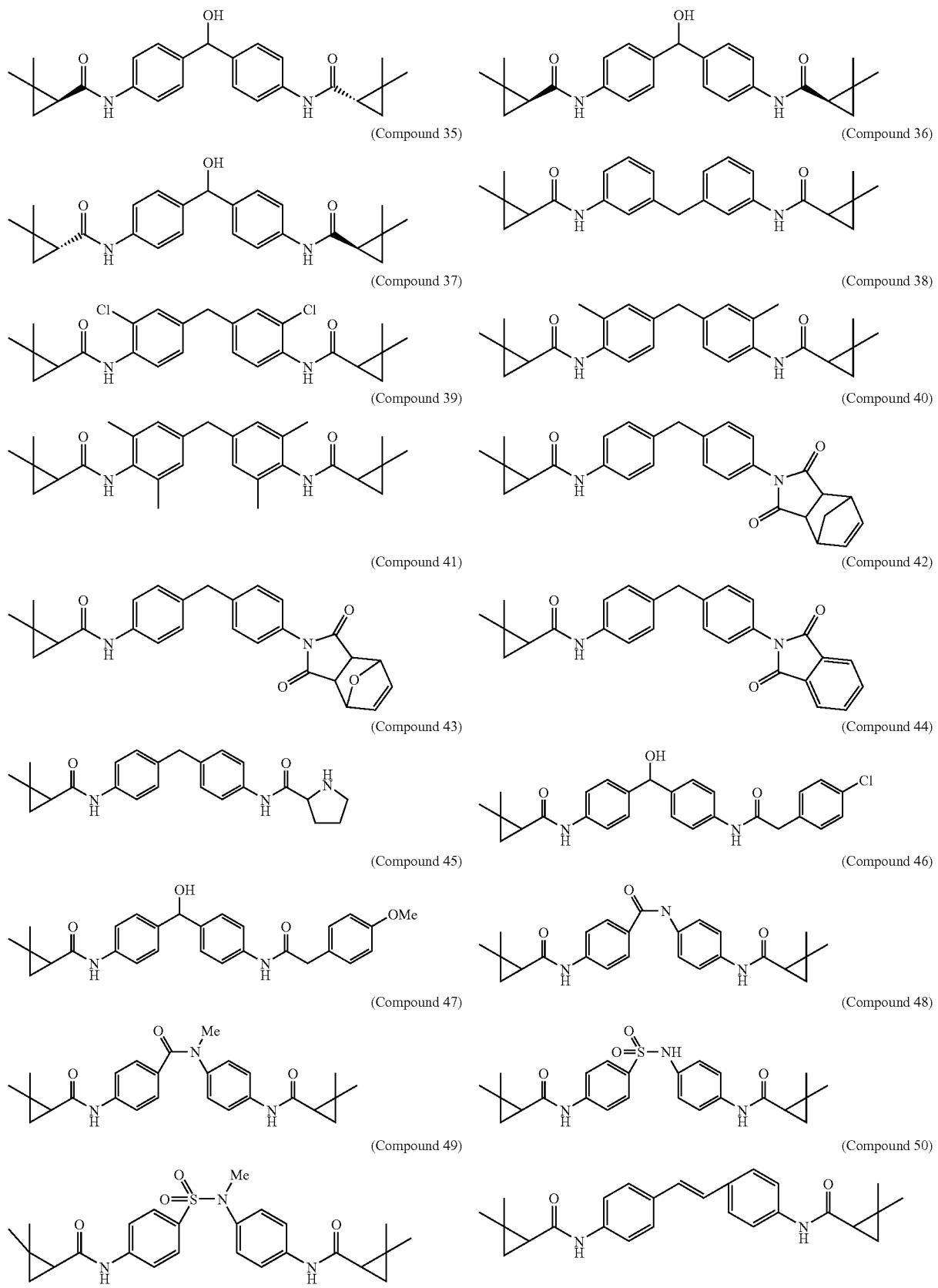

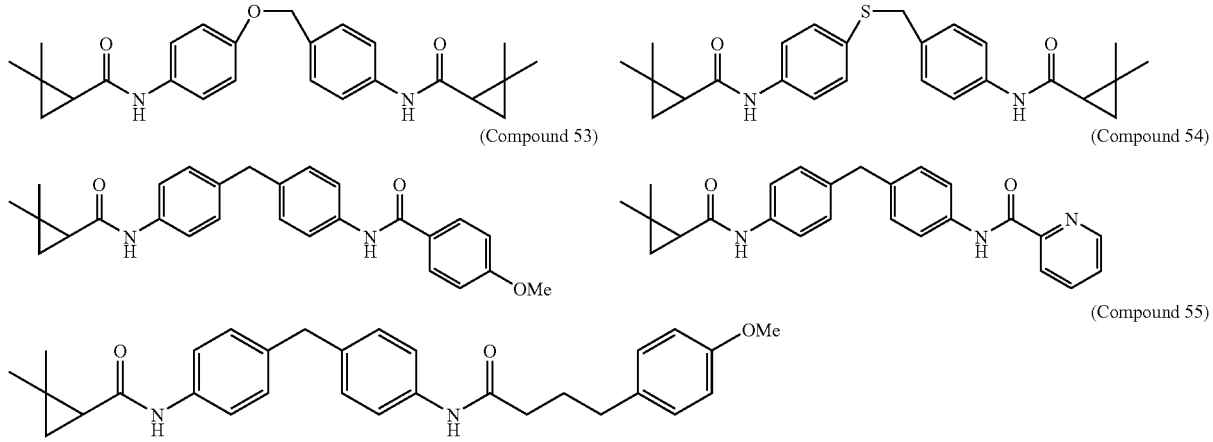

(Compound 51)
(Compound 52)
(Compound 53)
(Compound 54)
(Compound 55)

Example 1

Triethylamine (650 mg) and then 2,2-dimethylcychopropanecarboxylic acid chloride (860 mg) were added to a solution of 4,4'-diaminobenzophenone (500 mg) in dichloromethane (20 ml), and they were stirred at room temperature overnight. Water was added to the reaction mixture, and extracted with ethyl acetate, and the organic layer was washed with hydrochloric acid, water and saturated aqueous NaCl solution, then dried over anhydrous sodium sulfate and concentrated under reduced pressure. The obtained oily product was purified by silica gel column chromatography (hexane/ethyl acetate) to obtain compound 1 in the form of white crystals (668 mg).

MS(ESI) m/z 405 (M+H)$^+$ $^1$H-NMR(DMSO-d$_6$) δ=0.83 (2H, dd, J=7.8, 3.9 Hz), 1.01(2H, dd, J=5.7, 3.9 Hz), 1.15 (6H, s), 1.17(6H, s), 1.71(2H, dd, J=7.8, 5.7 Hz), 7.68(4H, d, J=9.0 Hz), 7.75(4H, d, J=9.0 Hz)

Example 2

Compound 2 was obtained in the form of white crystals (68 mg) from 4,4'-diaminodiphenyl sulfide (106 mg) in the same manner as that in Example 1.

MS(ESI) m/z 409 (M+H)$^+$ $^1$H-NMR(DMSO-d$_6$) δ=0.79 (2H, dd, J=7.8, 3.9 Hz), 0.97(2H, dd, J=5.1, 3.9 Hz), 1.13 (6H, s), 1.17(6H, s), 1.65(2H, dd, J=7.8, 5.1 Hz), 7.22(4H, d, J=8.7 Hz), 7.59(4H, d, J=8.7 Hz)

Example 3

Compound 3 was obtained in the form of brown crystals (64 mg) from 4,4'-diaminodiphenylamine sulfate (175 mg) in the same manner as that in Example 1.

MS(ESI) m/z 392 (M+H)$^+$ $^1$H-NMR(DMSO-d$_6$) δ=0.74 (2H, dd, J=7.8, 3.9 Hz), 0.94(2H, dd, J=5.1, 3.9 Hz), 1.14 (12H, s), 1.60(2H, dd, J=7.8, 5.1 Hz), 6.92(4H, d, J=8.7 Hz), 7.41(4H, d, J=8.7 Hz), 7.81(1H, s), 9.82(2H, s)

Example 4

Compound 4 was obtained in the form of white crystals (73 mg) from 4,4'-diaminodiphenyl ether (200 mg) in the same manner as that in Example 1.

MS(ESI) m/z 393 (M+H)$^+$ $^1$H-NMR(DMSO-d$_6$) δ=0.78 (2H, dd, J=7.8, 3.9 Hz), 0.96(2H, dd, J=5.7, 3.9 Hz), 1.15 (6H, s), 1.17(6H, s), 1.62(2H, dd, J=7.8, 5.7 Hz), 6.90(4H, d, J=8.7 Hz), 7.57(4H, d, J=8.7 Hz), 10.04(2H, s)

Example 5

Compound 5 was obtained in the form of white crystals (76 mg) from 4,4'-diaminodiphenyl sulfone (124 mg) in the same manner as that in Example 1.

MS(ESI) m/z 441 (M+H)$^+$ $^1$H-NMR(CDCl$_3$) δ=0.85-0.90 (2H, m), 1.18-1.26(14H, m), 1.39-1.46(2H, m), 7.60(2H, s), 7.64(4H, d, J=8.7 Hz), 7.83(4H, d, J=8.7 Hz)

Example 6

Compound 6 was obtained in the form of white crystals (404 mg) from 4,4'-ethylenedianiline (212 mg) in the same manner as that in Example 1.

MS(ESI) m/z 405 (M+H)$^+$ $^1$H-NMR(CDCl$_3$) δ=0.80-0.86 (2H, m), 1.15-1.28(14H, m), 1.37-1.43(2H, m), 2.87(4H, s), 7.09(4H, d, J=8.7 Hz), 7.32(2H, brs), 7.42(4H, d, J=8.7 Hz)

Example 7

Compound 7 was obtained in the form of white crystals (102 mg) from 3,4'-methylenedianiline (100 mg) in the same manner as that in Example 1.

MS(ESI) m/z 391 (M+H)$^+$ $^1$H-NMR(DMSO-d$_6$) δ=0.71-0.77(2H, m), 0.91-0.97(2H, m), 1.10-1.15(12H, m), 1.58-1.65(2H, m), 3.81(2H, s), 6.85(1H, d, J=7.2 Hz), 7.09(2H, d, J=8.1 Hz), 7.16(1H, t, J=8.1 Hz), 7.37(1H, s), 7.44(1H, d, J=8.1 Hz), 7.49(2H, d, J=8.1 Hz)

Example 8

The ketone compound (32 mg) obtained in Example 1 and hydroxylamine hydrochloride (38 mg) were dissolved in pyridine (3 ml), and the obtained solution was stirred at 100° C. overnight. Water was added to the reaction mixture and then the mixture was made acidic with hydrochloric acid. After the extraction with ethyl acetate, the extract was washed with hydrochloric acid, water and saturated aqueous NaCl solution, then dried over anhydrous sodium sulfate and concentrated under reduced pressure. Compound 8 (33 mg) was obtained in the form of yellow crystals.

MS(ESI) m/z 420 (M+H)$^+$ $^1$H-NMR(DMSO-d$_6$) δ=0.74-0.82(2H, m), 0.94-1.01(2H, m), 1.10-1.18(12H, m), 1.62-1.70(2H, m), 7.20(2H, d, J=8.7 Hz), 7.28(2H, d, J=8.7 Hz), 7.56(2H, d, J=8.7 Hz), 7.64(2H, d, J=8.7 Hz)

Example 9

Acetic anhydride (140 mg), pyridine (105 mg) and 4-N,N-dimethylaminopyridine (1 mg) were added to a solution of the oxime (30 mg) obtained in Example 8 in dichloromethane (3 ml), and they were stirred at room temperature overnight. Water was added to the reaction mixture and then the mixture was made acidic with hydrochloric acid. After the extraction with ethyl acetate, the extract was washed with water and saturated aqueous NaCl solution, then dried over anhydrous sodium sulfate and concentrated under reduced pressure to obtain O-acetyl oxime compound (38 mg) in the form of an yellow oil. This product was dissolved in methanol. Nickel dichloride hexahydrate (50 mg) and then sodium borohydride (30 mg)) were added to the obtained solution. They were stirred at room temperature for 30 minutes. After the addition of water followed by the extraction with ethyl acetate, the organic layer was washed with a saturated aqueous NaCl solution, dried over anhydrous sodium sulfate and concentrated under reduced pressure. The obtained oily product was purified by silica gel column chromatography (chloroform/methanol) to obtain compound 9 in the form of pale yellow crystals (28 mg).

MS(ESI) m/z 404 (M–H)$^-$ $^1$H-NMR(CDCl$_3$) δ=0.77-0.84 (2H, m), 1.15-1.22(14H, m), 1.36-1.43(2H, m), 5.11(1H, s), 7.25(4H, d, J=7.8 Hz), 7.43(2H, d, J=7.8 Hz)

Example 10

Acetic anhydride (70 mg), pyridine (70 mg) and 4-N,N-dimethylaminopyridine (1 mg) were added to a solution (3 ml) of the amine compound (22 mg) obtained in Example 9 in dichloromethane, and they were stirred at room temperature overnight. Water was added to the reaction mixture and then the obtained mixture was made acidic with hydrochloric acid. After the extraction with ethyl acetate, the extract was washed with water and saturated aqueous NaCl solution, then dried over anhydrous sodium sulfate and concentrated under reduced pressure. The obtained solid was purified with silica gel plate (developer: chloroform/methanol) to obtain compound 10 in the form of white crystals (6 mg).

MS(ESI) m/z 446 (M–H)$^-$ $^1$H-NMR(DMSO-d$_6$) δ=0.75 (2H, dd, J=7.5, 4.2 Hz), 0.95(2H, dd, J=5.4, 4.2 Hz), 1.11 (6H, s), 1.14(6H, s), 1.62(2H, d, J=7.5, 5.4 Hz), 5.96(1H, d, J=8.1 Hz), 7.12(4H, d, J=8.4 Hz), 7.50(2H, d, J=8.4 Hz), 8.62(1H, d, J=8.1 Hz)

Example 11

Sodium borohydride (15 mg) was added to a solution (5 ml) of the ketone compound (30 mg) obtained in Example 1 in ethanol, and they were stirred at room temperature overnight. Water was added to the reaction mixture and then ethanol was evaporated under reduced pressure. After the extraction with ethyl acetate, the extract was washed with saturated aqueous NaCl solution, then dried over anhydrous sodium sulfate and concentrated under reduced pressure. The obtained oily product was purified by silica gel column chromatography (hexane/ethyl acetate) to obtain compound 11 in the form of white crystals (30 mg).

MS(ESI) m/z 407 (M+H)$^+$ $^1$H-NMR(CDCl$_3$) δ=0.77-0.84 (2H, m), 1.13-1.23(14H, m), 1.40(2H, d, J=7.8, 5.4 Hz), 5.71(1H, s), 7.17-7.27(4H, m), 7.36-7.46(4H, m), 7.46-7.60 (2H, brs)

Example 12

One drop of concentrated sulfuric acid was added to a solution (5 ml) of the alcohol compound (35 mg) obtained in Example 11 in methanol, and they were stirred at room temperature for one hour. After the addition of water followed by the extraction of ethyl acetate, the extract was washed with saturated aqueous NaCl solution, then dried over anhydrous sodium sulfate and concentrated under reduced pressure to obtain compound 12 in the form of yellowish white crystals (35 mg).

MS(ESI) m/z 421 (M+H)$^+$ $^1$H-NMR(CDCl$_3$) δ=0.78-0.85 (2H, m), 1.16-1.23(14H, m), 1.35-1.41(2H, m), 3.34(3H, s), 5.16(1H, s), 7.24(4H, d, J=7.8 Hz), 7.35(2H, brs), 7.46(2H, d, J=7.8 Hz)

Example 13

Acetic anhydride (35 mg), pyridine (35 mg) and 4-N,N-dimethylaminopyridine (1 mg) were added to a solution (5 ml) of the alcohol compound (22 mg) obtained in Example 11 in dichloromethane, and they were stirred at room temperature overnight. Water was added to the reaction mixture and then the mixture was made acidic with hydrochloric acid. After the extraction with ethyl acetate, the extract was washed with water and saturated aqueous NaCl solution, then dried over anhydrous sodium sulfate and concentrated under reduced pressure. The obtained oily product was purified with silica gel plate (developer: hexane/ethyl acetate) to obtain compound 13 in the form of white crystals (22 mg).

MS(ESI) m/z 466 (M+NH$_4$)$^+$ $^1$H-NMR(CDCl$_3$) δ=0.82 (2H, d, J=7.8, 3.6 Hz), 1.16-1.23(14H, m), 1.40(2H, dd, J=5.4, 3.6 Hz), 2.13(3H, s), 6.79(1H, s), 7.23(4H, d, J=8.7 Hz), 7.40-7.52(2H, m)

Example 14

Sodium hydride (60% dispersion in mineral oil) (300 mg) was added to dimethyl sulfoxide (20 ml), and they were stirred at 70° C. for one hour. After cooling to room temperature, a solution (15 ml) of methyltriphenylphosphine bromide (2.68 g) in dimethyl sulfoxide was added to the reaction mixture. After stirring for 30 minutes, a solution (5 ml) of the ketone compound (250 mg) obtained in Example 1 in dimethyl sulfoxide was added to the reaction mixture and they were stirred at 100° C. overnight. After the addition of water followed by the extraction with ethyl acetate, the extract was washed with water and saturated aqueous NaCl solution, then dried over anhydrous sodium sulfate and concentrated under reduced pressure. The obtained oily product was purified by silica gel column chromatography (hexane/ethyl acetate) to obtain compound 14 in the form of yellowish white crystals (225 mg).

MS(ESI) m/z 403 (M+H)$^+$ $^1$H-NMR(DMSO-d$_6$) δ=0.78 (2H, dd, J=8.1, 3.9 Hz), 0.97(2H, dd, J=5.4, 3.9 Hz), 1.13 (6H, s), 1.15(6H, s), 1.65(2H, d, J=8.1, 5.4 Hz), 5.32(2H, s), 7.19(4H, d, J=8.7 Hz), 7.58(4H, d, J=8.7 Hz), 10.14(2H, s)

Example 15

Borane/tetrahydrofuran complex (1.0 M solution in tetrahydrofuran, 15 ml) was added to a solution (10 ml) of the methylene compound (600 mg) obtained in Example 14 in tetrahydrofuran, and they were stirred at room temperature for 2 hours. The resultant mixture was poured into water. After the extraction with ethyl acetate, the extract was washed with saturated aqueous NaCl solution, dried over anhydrous sodium sulfate and concentrated under reduced pressure. The obtained oily product was dissolved in ethanol (30 ml). A suspension (20 ml) of sodium hydroxide (3 g) in ethanol and then aqueous hydrogen peroxide solution (30%, 8 ml) were added to the obtained solution, and they were stirred at room temperature for 30 minutes. Water was added to the reaction mixture. Ethanol was evaporated under reduced pressure. After the extraction with ethyl acetate, the extract was washed with water and saturated aqueous NaCl solution, then dried over anhydrous sodium sulfate and concentrated under reduced pressure. The obtained oily product was purified by silica gel column chromatography (hexane/ethyl acetate) to obtain compound 15 in the form of white crystals (526 mg).

MS(ESI) m/z 421 (M+H)$^+$ $^1$H-NMR(DMSO-d$_6$) δ=0.74 (2H, dd, J=8.1, 4.2 Hz), 0.94(2H, dd, J=5.1, 4.2 Hz), 1.11 (6H, s), 1.13(6H, s), 1.61(2H, d, J=8.1, 5.1 Hz), 3.87(2H, d, J=4.2 Hz), 4.69(1H, t, J=4.2 Hz), 7.12(4H, d, J=8.4 Hz), 7.46(4H, d, J=8.4 Hz), 9.95(2H, s)

Example 16

Pyridine (140 mg), methane sulfonyl chloride (180 mg) and 4-N,N-dimethylaminopyridine (5 mg) were added to a solution (10 ml) of the hydroxymethyl compound (200 mg) obtained in Example 15 in dichloromethane, and they were stirred at room temperature overnight. Water was added to the obtained mixture. Dichloromethane was evaporated under reduced pressure. After the extraction with ethyl acetate, the extract was washed with an aqueous sodium hydrogencarbonate solution and saturated aqueous NaCl solution, dried over anhydrous sodium sulfate and concentrated under reduced pressure to obtain compound 16 in the form of yellow crystals (230 mg).

MS(ESI) m/z 499 (M+H)$^+$ $^1$H-NMR(CDCl$_3$) δ=0.78-0.86 (2H, m), 1.14-1.22(14H, m), 1.35-1.42(2H, m), 3.67(3H, s), 4.34(1H, t, J=7.5 Hz), 4.66(2H, d, J=7.5 Hz), 7.15(4H, d, J=8.1 Hz), 7.28(2H, brs), 7.46(4H, d, J=8.1 Hz)

Example 17

A suspension (2 ml) of sodium azide (22 mg) in N,N-dimethylformamide was added to a solution (3 ml) of the mesylate compound (31 mg) obtained in Example 16 in N,N-dimethylformamide, and hey were stirred at 100° C. for 6 hours. After the addition of water followed by the extraction with ethyl acetate, hexane in an mount equal to that of ethyl acetate was added to the obtained mixture. After washing with water and saturated aqueous NaCl solution, the extract was dried over anhydrous sodium sulfate and concentrated under reduced pressure to obtain compound 17 in the form of white crystals (26 mg).

MS(ESI) m/z 446 (M+H)$^+$ $^1$H-NMR(DMSO-d$_6$) δ=0.74 (2H, dd, J=7.8, 3.6 Hz), 0.94(2H, dd, J=5.1, 3.6 Hz), 1.11 (6H, s), 1.13(6H, s), 1.61(2H, dd, J=7.8, 5.1 Hz), 3.90(2H, d, J=8.1 Hz), 4.12(1H, t, J=8.1 Hz), 7.21(4H, d, J=8.4 Hz), 7.50(4H, d, J=8.4 Hz), 10.01(1H, s)

Example 18

Palladium/carbon (5%, 6 mg) was added to a solution (5 ml) of the azide compound (18 mg) obtained in Example 17 in ethanol, and they were stirred in hydrogen atmosphere at room temperature overnight. After the filtration, the filtrate was concentrated under reduced pressure. The obtained oily product was purified by silica gel column chromatography (chloroform/methanol) to obtain compound 18 in the form of white crystals (5 mg).

MS(ESI) m/z 420 (M+H)$^+$ $^1$H-NMR(CDCl$_3$) δ=0.78-0.84 (2H, m), 1.14-1.22(14H, m), 1.35-1.43(2H, m), 3.24(2H, d, J=7.5 Hz), 3.92(1H, t, J=7.5 Hz), 7.13(4H, d, J=8.1 Hz), 7.36-7.46(6H, m)

Example 19

A suspension (10 ml) of sodium cyanide (167 mg) in N,N-dimethylformamide was added to a solution (15 ml) of the mesylate compound (168 mg) obtained in Example 16 in N,N-dimethylformamide, and hey were stirred at 100° C. overnight. After the addition of water followed by the extraction with ethyl acetate, hexane in an mount equal to that of ethyl acetate was added to the obtained mixture. After washing with water and saturated aqueous NaCl solution, the extract was dried over anhydrous sodium sulfate and concentrated under reduced pressure to obtain compound 19 in the form of pale yellow crystals (139 mg).

MS(ESI) m/z 430 (M+H)$^+$ $^1$H-NMR(DMSO-d$_6$) δ=0.74-0.82(2H, m), 0.94-1.02(2H, m), 1.12(6H, s), 1.15(6H, s), 1.60-1.70(2H, m), 3.24(2H, d, J=7.8 Hz), 4.28(1H, t, J=7.8 Hz), 7.23(4H, d, J=8.1 Hz), 7.52(2H, d, J=8.1 Hz), 10.04 (2H, s)

Example 20

An aqueous sodium hydroxide solution (2 N, 0.5 ml) was added to a. solution (5 ml) of the cyano compound (60 mg) obtained in Example 19 in ethanol, and they were heated under reflux overnight. Ethanol was evaporated under reduced pressure. Water was added to the residue. After washing with ethyl acetate, the aqueous layer was made acidic with hydrochloric acid. After the extraction with ethyl acetate, the extract was washed with water and saturated aqueous NaCl solution, dried over anhydrous sodium sulfate and concentrated under reduced pressure to obtain compound 20 in the form of pale yellow crystals (9 mg).

MS(ESI) m/z 449 (M+H)$^+$ $^1$H-NMR(CDCl$_3$) δ=0.78-0.84 (2H, m), 1.12-1.30(14H, m), 1.36-1.42(2H, m), 3.00(2H, d, J=7.5 Hz), 4.44(1H, t, J=7.5 Hz), 7.11(4H, d, J=8.1 Hz), 7.40(4H, d, J=8.1 Hz), 7.49(2H, brs)

Example 21

A solution (3 ml) of m-chloroperbenzoic acid (9 mg) in chloroform was dropped into a solution (3 ml) of the sulfide compound (20 mg) obtained in Example 2 in chloroform under cooling with ice, and they were stirred for 3 hours. After the addition of water followed by the extraction with ethyl acetate, the obtained extract was washed with saturated aqueous sodium hydrogencarbonate solution and saturated aqueous NaCl solution. The product was dried over anhydrous sodium sulfate and concentrated under reduced pressure. The obtained oily product was purified by silica gel column chromatography (hexane/ethyl acetate) to obtain compound 21 in the form of white crystals (16 mg).

MS(ESI) m/z 425 (M+H)$^+$ $^1$H-NMR(CDCl$_3$) δ=0.83(2H, d, J=7.8, 3.9 Hz), 1.14-1.23(14H, m), 1.47(2H, dd, J=7.8, 5.1 Hz), 7.47(4H, d, J=8.7 Hz), 7.62(4H, d, J=8.7 Hz), 8.17 (2H, s)

Example 22

Triethylamine (1.73 ml) and then 2,2-dimethylcyclopropanecarboxylic acid chloride (1.18 g) were added to a solution of 4,4'-diaminodiphenylmethane (3.51 g) in dichloromethane, and they were stirred at room temperature for 15 minutes. Water was added to the obtained mixture. Dichloromethane was evaporated under reduced pressure. After the extraction with ethyl acetate, the extract was washed with water and saturated aqueous NaCl solution, dried over anhydrous sodium sulfate and concentrated under reduced pressure. The obtained oily product was purified by silica gel column chromatography (hexane/ethyl acetate) to obtain compound 22 in the form of white crystals (1.02 g).

$^1$H-NMR(CDCl$_3$) δ=0.78-0.85(1H, m), 1.16-1.24(7H, m), 1.34-1.50(1H, m), 3.55(2H, brs), 3.82(2H, s), 6.62(2H, d, J=8.4 Hz), 6.95(2H, d, J=8.4 Hz), 7.11(2H, d, J=8.4 Hz), 7.22(1H, brs), 7.42(2H, d, J=8.4 Hz)

Example 23

Triethylamine (26 mg), 2,2-dichlorocyclopropanecarboxylic acid chloride (35 mg) and 4-N,N-dimethylaminopyridine (1 mg) were added to a solution (5 ml) of the monoacyl compound (50 mg) obtained in Example 22 in dichloromethane, and they were stirred at room temperature overnight. Water was added to the obtained mixture. After the extraction with ethyl acetate, the extract was washed with saturated aqueous sodium hydrogencarbonate solution and saturated aqueous NaCl solution, dried over anhydrous sodium sulfate and concentrated under reduced pressure. The obtained oily product was purified with silica gel plate (developer: hexane/ethyl acetate) to obtain compound 23 in the form of white crystals (8 mg).

MS(ESI) m/z 431 (M+H)$^+$ $^1$H-NMR(DMSO-d$_6$) δ=0.74 (1H, dd, J=7.8, 3.9 Hz), 0.94(2H, dd, J=5.1, 3.9 Hz), 1.12 (3H, s), 1.14(3H, s), 1.62(1H, dd, J=7.8, 5.1 Hz), 2.00(2H, d, J=9.2 Hz), 2.83(1H, t, J=9.2 Hz), 3.82(2H, s), 7.08(2H, d, J=8.4 Hz), 7.13(2H, d, J=8.4 Hz), 7.47(2H, d, J=8.4 Hz), 7.51(2H, d, J=8.4 Hz), 9.96(1H, s), 10.50(1H, s)

Example 24

Compound 24 (34 mg) was obtained in the form of yellowish white crystals from the monoacyl compound (40 mg) obtained in Example 22 and 4-methoxyphenylacetic acid chloride in the same manner as that in Example 23.

MS(ESI) m/z 443 (M+H)$^+$ $^1$H-NMR(DMSO-d$_6$) δ=0.74 (1H, dd, J=7.5, 3.9 Hz), 0.94(1H, dd, J=5.1, 3.9 Hz), 1.11 (3H, s), 1.13(3H, s), 1.61(1H, dd, J=7.5, 5.1 Hz), 3.50(2H, s), 3.72(3H, s), 3.78(2H, s), 6.86(2H, d, J=8.7 Hz), 7.07(2H, d, J=8.4 Hz), 7.09(2H, d, J=8.4 Hz), 7.22(2H, d, J=8.4 Hz), 7.47(4H, d, J=8.4 Hz), 9.96(1H, s), 10.01(1H, s)

Example 25

Compound 25 (26 mg) was obtained in the form of brown crystals from the monoacyl compound (40 mg) obtained in Example 22 and 4-dimethylaminophenylacetic acid chloride in the same manner as that in Example 23.

MS(ESI) m/z 443 (M+H)$^+$ $^1$H-NMR(DMSO-d$_6$) δ=0.74 (1H, dd, J=7.5, 3.9 Hz), 0.94(2H, dd, J=5.1, 3.9 Hz), 1.11 (3H, s), 1.13(3H, s), 1.61(2H, dd, J=7.5, 5.1 Hz), 2.83(6H, s), 3.43(2H, s), 3.80(2H, s), 6.66(2H, d, J=8.4 Hz), 7.05-7.16 (6H, m), 7.47(4H, d, J=8.4 Hz), 9.95(1H, s), 9.97(1H, s)

Example 26

4-Methoxydihydrocinnamic acid (30 mg), WSC.HCl (31 mg), HOBT.H2O (25 mg), triethylamine (21 mg) and 4-N,N-dimethylaminopyridine (1 mg) were added to a solution (5 ml) of the monoacyl compound (40 mg) obtained in Example 22 in N,N-dimethylformamide, and they were stirred at 70° C. overnight. Water was added to the obtained mixture. After the extraction with ethyl acetate, the extract was washed with hydrochloric acid, saturated aqueous sodium hydrogencarbonate solution, water and saturated aqueous NaCl solution, dried over anhydrous sodium sulfate and concentrated under reduced pressure. The obtained oily product was purified with silica gel plate (developer: hexane/ethyl acetate) to obtain compound 26 in the form of brown crystals (4 mg).

MS(ESI) m/z 457 (M+H)$^+$ $^1$H-NMR(CDCl$_3$) δ=0.78-0.85 (1H, m), 1.16-1.24(7H, m), 1.35-1.42(1H, m), 2.60(2H, t, J=7.5 Hz), 2.98(2H, t, J=7.5 Hz), 3.78(3H, s), 3.88(2H, s), 6.83(2H, d, J=8.7 Hz), 6.97(1H, s), 7.06-7.17(6H, m), 7.33 (2H, d, 8.4 Hz), 7.42(2H, d, J=8.4 Hz)

Example 27

1-Bromo-2-(4-methoxyphenyl)ethane, potassium carbonate and sodium iodide were added to a solution (5 ml) of the monoacyl compound (40 mg) obtained in Example 22 in N,N-dimethylformamide, and they were stirred at 70° C. for two days. Water was added to the obtained mixture. After the extraction with ethyl acetate, the extract was washed with water and saturated aqueous NaCl solution, dried over anhydrous sodium sulfate and concentrated under reduced pressure. The obtained oily product was purified with silica gel plate (developer: hexane/ethyl acetate) to obtain compound 27 in the form of white crystals (3 mg).

MS(ESI) m/z 429 (M+H)$^+$ $^1$H-NMR(CDCl$_3$) δ=0.78-0.85 (1H, m), 1.16-1.24(7H, m), 1.35-1.42(1H, m), 2.84(2H, t, J=6.9 Hz), 3.33(2H, t, J=6.9 Hz), 3.80(3H, s), 3.83(2H, s), 6.54(2H, d, J=8.4 Hz), 6.85(2H, d, J=8.4 Hz), 6.97(2H, d, J=8.4 Hz), 7.07-7.15(4H, m), 7.21(1H, s), 7.42(2H, d, J=8.4 Hz)

Example 28

Compound 28 (4 mg) was obtained in the form of white crystals from the monoacyl compound (10 mg) obtained in Example 22 and 1-bromo-3-(4-methoxyphenyl)propane in the same manner as that in Example 27.

MS(ESI) m/z 443 (M+H)$^+$ $^1$H-NMR(CDCl$_3$) δ=0.78-0.85 (1H, m), 1.16-1.24(7H, m), 1.35-1.42(1H, m), 1.90(2H, qui, J=6.9 Hz), 2.67(2H, t, J=6.9 Hz), 3.11(2H, t, J=6.9 Hz), 3.79(3H, s), 3.82(2H, s), 6.51(2H, d, J=8.4 Hz), 6.83(2H, d, J=8.4 Hz), 6.96(2H, d, J=8.4 Hz), 7.11(4H, d, J=8.4 Hz), 7.22(1H, s), 7.40(2H, d, J=8.4 Hz)

Examples 29 and 30

Triethylamine (140 mg), (S)-2,2-dimethylcyclopropanecarboxylic acid chloride (92 mg) and 4-N,N-dimethylaminopyridine (1 mg) were added to a solution (5 ml) of 4,4'-diaminobenzophenone (96 mg) in dichloromethane, and they were stirred at room temperature for 2 hours. Water was added to the obtained mixture. After the extraction with ethyl acetate, the extract was washed with hydrochloric acid, water and saturated aqueous NaCl solution, dried over anhydrous sodium sulfate and concentrated under reduced pressure. The obtained oily product was purified by silica gel column chromatography (hexane/ethyl acetate) to obtain compound 29 in the form of pale yellow crystals (50 mg) and compound 30 also in the form of pale yellow crystals (46 mg).

The characteristic data of compound 29 were as follows:
MS(ESI) m/z 405 (M+H)$^+$ $^1$H-NMR(DMSO-d$_6$) δ=0.79 (2H, dd, J=7.8, 3.9 Hz), 0.97(2H, dd, J=5.1, 3.9 Hz), 1.13 (6H, s), 1.17(6H, s), 1.65(2H, dd, J=7.8, 5.1 Hz), 7.22(4H, d, J=8.7 Hz), 7.59(4H, d, J=8.7 Hz)

The characteristic data of compound 30 were as follows:
MS(ESI) m/z 309 (M+H)$^+$ $^1$H-NMR(CDCl$_3$) δ=0.89(1H, d, J=8.1, 4.2 Hz), 1.21-1.29(7H, m), 1.43(1H, d, J=8.1, 5.7 Hz), 4.10(2H, brs), 6.67(2H, d, J=8.4 Hz), 7.45(1H, brs), 7.61(2H, d, J=8.4 Hz), 7.69(2H, d, J=8.4 Hz), 7.74(2H, d, J=8.4 Hz)

Example 31

Triethylamine (14 mg), (R)-2,2-dimethylcyclopropanecarboxylic acid chloride (19 mg) and 4-N,N-dimethylaminopyridine (1 mg) were added to a solution (3 ml) of compound 30 (34 mg) obtained in Example 30 in dichloromethane and they were stirred at room temperature for 2 hours. Water was added to the obtained mixture. After the extraction with ethyl acetate, the extract was washed with hydrochloric acid, water and saturated aqueous NaCl solution, dried over anhydrous sodium sulfate and concentrated under reduced pressure to obtain compound 31 in the form of pale yellow oil (45 mg).

Example 32

Triethylamine (70 mg), (R)-2,2-dimethylcyclopropanecarboxylic acid chloride (81 mg) and 4-N,N-dimethylaminopyridine (1 mg) were added to a solution (3 ml) of 4,4'-diaminobenzophenone (50 mg) in dichloromethane and they were stirred at room temperature for 2 hours. Water was added to the obtained mixture. After the extraction with ethyl acetate, the extract was washed with hydrochloric acid, water and saturated aqueous NaCl solution, dried over anhydrous sodium sulfate and concentrated under reduced pressure to obtain compound 32 in the form of pale yellow crystals (94 mg).

Example 33

Sodium borohydride (10 mg) was added to a solution (3 ml) of compound 29 (46 mg) obtained in Example 29 in ethanol, and they were stirred at room temperature for 3 hours. Water was added to the obtained mixture. After the evaporation of ethanol under reduced pressure followed by the extraction with ethyl acetate, the extract was washed with saturated aqueous NaCl solution, dried over anhydrous sodium sulfate and concentrated under reduced pressure. The obtained solid was purified with silica gel plate (developer: hexane/ethyl acetate) to obtain compound 33 in the form of yellowish white crystals (43 mg).
MS(ESI) m/z 407 (M+H)$^+$[α]D+76.4° (c=0.76, CHCl$_3$)

Example 34

Sodium borohydride (15 mg) was added to a solution (3 ml) of the ketone compound (63 mg) obtained in Example 31 in ethanol, and they were stirred at room temperature for 3 hours. Water was added to the obtained mixture. After the evaporation of ethanol under reduced pressure followed by the extraction with ethyl acetate, the extract was washed with saturated aqueous NaCl solution, dried over anhydrous sodium sulfate and concentrated under reduced pressure. The obtained solid was purified with silica gel plate (developer: hexane/ethyl acetate) to obtain compound 34 in the form of yellowish white crystals (41 mg).
MS(ESI) m/z 407 (M+H)$^+$ Example 35

Sodium borohydride (20 mg) was added to a solution (4 ml) of the ketone compound (88 mg) obtained in Example 32 in ethanol, and they were stirred at room temperature for 3 hours. Water was added to the obtained mixture. After the evaporation of ethanol under reduced pressure followed by the extraction with ethyl acetate, the extract was washed with saturated aqueous NaCl solution, dried over anhydrous sodium sulfate and concentrated under reduced pressure. The obtained solid was purified with silica gel plate (developer: hexane/ethyl acetate) to obtain compound 35 in the form of yellowish white crystals (70 mg).
MS(ESI) m/z 407 (M+H)$^+$[α]D−78.2° (c=1.31, CHCl$_3$)

Example 36

Compound 36 was obtained in the form of white crystals (162 mg) from 3,3'-diaminodiphenylmethane (100 mg) in the same manner as that in Example 1.
MS(ESI) m/z 391 (M+H)$^+$ $^1$H-NMR(DMSO-d$_6$) δ=0.74 (2H, dd, J=3.9, 7.5 Hz), 0.94(2H, dd, J=3.9, 5.7 Hz), 1.11 (6H, s), 1.13(6H, s), 1.62(2H, dd, J=5.7, 7.5 Hz), 3.82(2H, s), 6.86(2H, d, J=7.2 Hz), 7.17(2H, t, J=8.1 Hz), 7.38(2H, s), 7.46(2H, d, J=8.4 Hz)

Example 37

Compound 37 was obtained in the form of white crystals (16 mg) from 4,4'-diamino-3,3'-dichlorodiphenylmethane (50 mg) in the same manner as that in Example 1.
MS(ESI) m/z 459 (M+H)$^+$ $^1$H-NMR(DMSO-d$_6$) δ=0.74-0.80(2H, m), 0.93-0.97(2H, m), 1.14(6H, s), 1.15(6H, s), 1.79-1.86(2H, m), 3.88(2H, s), 7.17(2H, dd, J=2.1, 8.1 Hz), 7.36(2H, t, J=2.1 Hz), 7.58(2H, d, J=8.1 Hz), 9.50-9.56 (2H, brs)

Example 38

Compound 38 was obtained in the form of white crystals (29 mg) from 4,4'-diamino-3,3'-dimethyldiphenylmethane (50 mg) in the same manner as that in Example 1.
MS(ESI) m/z 419 (M+H)$^+$ $^1$H-NMR(DMSO-d$_6$) δ=0.70-0.75(2H, m), 0.91-0.96(2H, m), 1.14(6H, s), 1.15(6H, s), 1.69-1.75(2H, m), 2.14(6H, s), 3.89(2H, s), 6.97(2H, d, J=8.1 Hz), 7.02(2H, s), 7.24(2H, d, J=8.1 Hz), 9.28-9.34(2H, brs)

Example 39

Compound 39 was obtained in the form of white crystals (63 mg) from 4,4'-diamino-3,3',5,5'-tetramethyldiphenylmethane (50 mg) in the same manner as that in Example 1.
MS(ESI) m/z 447 (M+H)$^+$ $^1$H-NMR(DMSO-d$_6$) δ=0.69-0.75(2H, m), 0.90-0.95(2H, m), 1.13(6H, s), 1.16(6H, s), 1.65-1.72(2H, m), 2.08(12H, s), 3.73(2H, s), 6.88(4H, s), 9.22(2H, s)

Example 40

Compound 40 was obtained in the form of white crystals (36 mg) from N-[4-(4-aminobenzyl)phenyl]-5-norbornene-2,3-dicarboxamide (105 mg) and 1.3 equivalents of dimethylcyclopropanecarboxylic acid chloride in the same manner as that in Example 1.

MS(ESI) m/z 441 (M+H)+ 1H-NMR(CDCl$_3$) δ=0.82(1H, dd, J=5.0, 7.8 Hz), 1.19-1.26(7H, m), 1.38(1H, dd, J=5.1, 8.1 Hz), 1.60(1H, d, J=8.7 Hz), 1.78(1H, d, J=8.7 Hz), 3.41(2H, m), 3.49(2H, m), 6.24(2H, t, J=1.8 Hz), 7.03(2H, d, J=8.4 Hz), 7.11(2H, d, J=8.1 Hz), 7.21(2H, d, J=8.4 Hz), 7.43(1H, d, J=7.8 Hz)

Example 41

Compound 41 was obtained in the form of white crystals (15 mg) from the monoacyl compound (60 mg) obtained in Example 22 and exo-3,6-epoxy-1,2,3,6-tetrahydrophthalic anhydride (93 mg) in the same manner as that in Example 23.

MS(ESI) m/z 443 (M+H)+ 1H-NMR(CDCl$_3$) δ=0.82(1H, dd, J=3.9, 7.2 Hz), 1.18-1.28(7H, m), 1.38(1H, dd, J=5.1, 8.1 Hz), 3.00(2H, s), 5.38(2H, t, J=0.9 Hz), 6.56(2H, t, J=0.9 Hz), 7.11(2H, d, J=8.1 Hz), 7.16(2H, d, J=6.3 Hz), 7.24(2H, d, J=6.3 Hz), 7.29(1H, s), 7.44(2H, d, J=8.1 Hz)

Example 42

Compound 42 was obtained in the form of white crystals (21 mg) from the monoacyl compound (15 mg) obtained in Example 22 and phthalic anhydride (8 mg) in the same manner as that in Example 23.

MS(ESI) m/z 425 (M+H)+ 1H-NMR(CDCl$_3$) δ=0.82(1H, dd, J=3.9, 7.2 Hz), 1.18-1.28(7H, m), 1.35-1.40(1H, m), 3.99 (2H, s), 7.18(2H, d, J=8.1 Hz), 7.30(2H, d, J=8.4 Hz), 7.34 (2H, d, J=8.4 Hz), 7.45(2H, d, J=8.1 Hz), 7.79(2H, dd, J=5.7, 3.3 Hz), 7.95(2H, dd, J=5.7, 3.3 Hz).

Example 43

Compound 43 was obtained in the form of white crystals by condensing the monoacyl compound obtained in Example 22 with N-benzyloxycarbonylproline in the same manner as that in Example 26 and then removing the protecting group by the reduction with palladium.

MS(ESI) m/z 392 (M+H)+

Example 44

A monoamide compound (626 mg) was obtained from 4,4'-diaminobenzophenone (3.5 g) and dimethylcyclopropanecarboxylic acid chloride (2.63 g) in the same manner as that of Examples 29 and 30. An asymmetric diamide compound was obtained from the resultant monoamide (42 mg) and 4-chlorophenylacetoyl chloride (64 mg) in the same manner as that of Example 23. This product was reduced with sodium borohydride in the same manner as that of Example 11 to obtain compound 44 in the form of white crystals (43 mg).

MS(ESI) m/z 463 (M+H)+ 1H-NMR(DMSO-d$_6$) δ=0.75 (1H, dd, J=7.5, 3.9 Hz), 0.94(1H, dd, J=5.1, 3.9 Hz), 1.12 (3H, s), 1.14(3H, s), 1.60-1.65(1H, m), 3.61(2H, s), 5.57(1H, d, J=3.9 Hz), 5.70(1H, d, J=3.9 Hz), 7.20-7.30(4H, m), 7.34 (2H, d, J=8.4 Hz), 7.38(2H, d, J=8.4 Hz), 7.50(4H, d, J=8.0 Hz), 9.96(1H, s), 10.11(1H, s)

Example 45

Compound 45 was obtained in the form of white crystals (48 mg) from the obtained monoamide (42 mg) and 4-methoxyphenylacetoyl chloride (126 mg) in the same manner as that in Example 43.

MS(ESI) m/z 459 (M+H)+ 1H-NMR(DMS1-d$_6$) δ=0.75 (1H, dd, J=7.5, 3.9 Hz), 0.95(1H, dd, J=5.1, 3.9 Hz), 1.12 (3H, s), 1.14(3H, s), 1.62(1H, dd, J=7.5, 5.1 Hz), 3.50(2H, s), 3.72(3H, s), 5.57(1H, d, J=4.2 Hz), 5.70(1H, d, J=4.2 Hz), 6.86(2H, d, J=8.7 Hz), 7.10-7.30(6H, m), 7.50(4H, d, J=8.4 Hz), 9.98(1H, s), 10.03(1H, s)

Example 46

Compound 46 was obtained from N-(4-aminophenyl)carbamoylaniline in the same manner as that in Example 1.

MS(ESI) m/z 420 (M+H)+ 1H-NMR(DMSO-d$_6$) δ=0.73-0.88(2H, m), 0.94-1.02(2H, m), 1.13(3H, s), 1.15(6H, s), 1.17(3H, s), 1.58-1.72(2H, m), 7.54(2H, d, J=8.7 Hz), 7.64 (2H, d, J=8.7 Hz), 7.71(2H, d, J=8.7 Hz), 7.90(2H, d, J=8.7 Hz), 10.00(2H, s), 10.34(1H, s)

Example 47

Compound 47 was obtained from N-(4-aminophenyl)-N-methylcarbamoylaniline in the same manner as that in Example 1.

MS(ESI) m/z 434 (M+H)+ 1H-NMR(CDCl$_3$) δ=0.77-0.84 (2H, m), 1.15(3H, s), 1.16(3H, s), 1.19(3H, s), 1.21(3H, s), 1.39-1.46(2H, m), 1.68-1.73(2H, m), 3.44(3H, s), 6.92(2H, d, J=8.7 Hz), 7.20(2H, d, J=8.7 Hz), 7.28(2H, d, J=8.7 Hz), 7.36(2H, d, J=8.7 Hz), 7.80-7.88(1H, brs), 7.91-8.03(1H, brs)

Example 48

Compound 48 was obtained from N-(4-aminophenyl)sulfonyl-p-phenylenediamine in the same manner as that in Example 1.

MS(ESI) m/z 456 (M+H)+ 1H-NMR(DMSO-d$_6$) δ=0.78-0.88(2H, m), 0.92-1.02(2H, m), 1.08-1.18(12H, m), 1.63-1.72(2H, m), 6.95(2H, d, J=8.7 Hz), 7.41(2H, d, J=8.7 Hz), 7.59(2H, d, J=8.7 Hz), 7.69(2H, d, J=8.7 Hz), 9.88(1H, s), 9.95(1H, s), 10.40(1H, s)

Example 49

Compound 49 was obtained from N-(4-aminophenyl)sulfonyl-N-methyl-phenylenediamine in the same manner as that in Example 1.

MS(ESI) m/z 470 (M+H)+ 1H-NMR(DMSO-d$_6$) δ=0.76-0.86(2H, m), 0.92-1.02(2H, m), 1.11-1.19(12H, m), 1.60-1.72(2H, m), 3.05(3H, s), 6.97(2H, d, J=8.7 Hz), 7.16(2H, d, J=8.7 Hz), 7.40(2H, d, J=8.7 Hz), 7.52(2H, d, J=8.7 Hz), 10.12(1H, s), 10.18(1H, s)

Example 50

Compound 50 was obtained from 4,4'-diaminostilbene in the same manner as that in Example 1.

MS(ESI) m/z 402 (M+H)+ 1H-NMR(DMSO-d$_6$) δ=0.79 (2H, dd, J=7.8, 3.9 Hz), 0.98(2H, dd, J=5.7, 3.9 Hz), 1.16 (6H, s), 1.17(6H, s), 1.66(2H, dd, J=7.8, 5.7 Hz), 7.06(2H, s), 7.48(4H, d, J=9.0 Hz), 7.60(4H, d, J=9.0 Hz), 10.12(2H, s)

Example 51

Compound 51 was obtained from 4-(4-aminobenzyloxy)aniline in the same manner as that in Example 1.

MS(ESI) m/z 407 (M+H)+ 1H-NMR(DMSO-d$_6$) δ=0.72-0.80(2H, m), 0.92-1.00(2H, m), 1.13(3H, s), 1.14(6H, s), 1.16(3H, s), 1.57-1.68(2H, m), 4.96(2H, s), 6.91(2H, d, J=9.0 Hz), 7.33(2H, d, J=8.4 Hz), 7.48(2H, d, J=9.0 Hz), 7.59(2H, d, J=8.4 Hz), 9.89(1H, s), 10.08(1H, s)

Example 52

Compound 52 was obtained from 4-(4-aminobenzylthio) aniline in the same manner as that in Example 1.
MS(ESI) m/z 423 (M+H)$^+$ $^1$H-NMR(DMSO-d$_6$) δ=0.74-0.80(2H, m), 0.93-0.99(2H, m), 1.13(6H, s), 1.15(6H, s), 1.58-1.65(2H, m), 4.08(2H, s), 7.18(2H, d, J=8.4 Hz.), 7.24 (2H, d, J=8.4 Hz), 7.48(2H, d, J=8.4 Hz), 7.52(2H, d, J=8.4 Hz), 10.02(1H, s), 10.09(1H, s)

Example 53

Compound 53 was obtained from the monoacyl compound obtained in Example 22 and 4-methoxybenzoyl chloride in the same manner as that in Example 23.
MS(ESI) m/z 429 (M+H)$^+$ $^1$H-NMR(DMSO-d$_6$) δ=0.74-0.78(1H, m), 0.94-0.98(1H, m), 1.13-1.15(6H, m), 1.60-1.66 (1H, m), 3.84(5H, s), 7.03-7.17(6H, m), 7.49(2H, d, J=8.4 Hz), 7.66(2H, d, J=8.4 Hz), 7.95(2H, d, J=8.4 Hz), 9.95 (1H, s), 10.02(1H, s)

Example 54

Compound 54 was obtained from the monoacyl compound obtained in Example 22 and 2-pyridinecarboxylic acid chloride in the same manner as that in Example 23.
MS(ESI) m/z 400 (M+H)$^+$ $^1$H-NMR(CDCl$_3$) δ=0.76-0.82 (1H, m), 1.16-1.26(7H, m), 1.36-1.42(1H, m), 3.92(2H, s), 7.12(2H, d, J=8.4 Hz), 7.18(2H, d, J=8.4 Hz), 7.43-7.49(4H, m), 7.69(2H, d, J=8.4 Hz), 7.89(2H, t, J=8.4 Hz), 8.28(1H, d, J=8.4 Hz), 8.59(1H, d, J=5.4 Hz), 9.98(1H, s)

Example 55

Compound 55 was obtained from the monoacyl compound obtained in Example 22 and 4-(4-methoxyphenyl)butanoyl chloride in the same manner as that in Example 23.
MS(ESI) m/z 471 (M+H)$^+$ $^1$H-NMR(CDCl$_3$) δ=0.80-0.85 (1H, m), 1.18-1.24(7H, m), 1.36-1.41(1H, m), 2.03(2H, quint., J=7.5 Hz), 2.31(2H, t, J=7.5 Hz), 2.65(2H, t, J=7.5 Hz), 3.78(3H, s), 3.89(2H, s), 6.83(2H, d, J=8.4 Hz), 6.98-6.99(1H, m), 7.11(6H, d, J=8.4 Hz), 7.21-7.22(1H, m), 7.37-7.43(3H, m)

Example 56

Evaluation of AP-1 Inhibition:
Cells used for the tests were those prepared by stably introducing *E. coli* β-galactosidase (β-gal) genes driven by SV 40 minimum promoter fused with 4 tandems of the AP-1 binding motif derived from human MMP-1 gene enhancer into human normal umbilical cord vein endothelial cells (HU-VEC) immortalized with SV 40 large T antigen. The cells were subcultured in RPMI medium containing 10% of FBS, and were seeded on a 96-well plate in a concentration of 1×10$^4$/well on a day before the start of the experiments. A compound of the present invention was dissolved in DMSO to obtain a solution of a proper concentration, which was added into the 96-well plate so that the final DMSO concentration would be not higher than 1%. 30 minutes after the addition of the compound, phorbol-12-myristate-13-acetate (PMA) was added to each well so as to obtain the final concentration of 50 ng/ml. β-gal activity was determined 16 hours after with a chemiluminescent substrate (Galacton-Light-Plus: Boehringer Mannheim) according to a protocol attached to the reagent. A Luminescence detector (ATTO) was used for the determination. In this evaluation system, β-gal activity induced by PMA was substantially completely inhibited by glucocorticoid which is a known AP-1 inhibitor.

The compounds obtained in Examples 1 to 55 exhibited the inhibition effect in these tests.

Example 57

Evaluation of NF-Kappa B Inhibition:
The tests were carried out in the same manner as that of Example 56. Concretely, the AP-1 binding motif of the reporter genes in Example 56 was replaced with the NF-kappa B binding motif derived from immunoglobulin kappa light chain enhancer, and NF-kappa B transcriptional activity was induced with 1 ng/ml of IL-1β in place of PMA. In this evaluation system, β-gal activity induced by IL-1β was substantially completely inhibited by glucocorticoid which is a known NF-kappa B inhibitor.

The results of the evaluation are shown in Table 1.

TABLE 1

| Tested compound | NF-kB inhibiting activity IC50 (ug/ml) |
|---|---|
| Compound 1 | >5.0 |
| Compound 2 | 0.1 |
| Compound 3 | 1 |
| Compound 4 | 1.1 |
| Compound 5 | >5.0 |
| Compound 6 | 0.37 |
| Compound 7 | 0.37 |
| Compound 8 | 5 |
| Compound 9 | 2.5 |
| Compound 10 | >5.0 |
| Compound 11 | 0.12 |
| Compound 12 | >5.0 |
| Compound 13 | 0.12 |
| Compound 14 | >5.0 |
| Compound 15 | 0.62 |
| Compound 16 | 2.5 |
| Compound 17 | 2.5 |
| Compound 18 | 3 |
| Compound 19 | 1.2 |
| Compound 20 | 3 |
| Compound 23 | 0.1 |
| Compound 24 | 0.1 |
| Compound 25 | 0.03 |
| Compound 26 | 0.1 |
| Compound 27 | 0.1 |
| Compound 28 | 0.1 |
| Compound 34 | 0.06 |
| Compound 35 | >5.0 |
| Compound 38 | 0.5 |
| Compound 40 | 1 |
| Compound 43 | 0.1 |
| Compound 44 | 1.5 |
| Compound 45 | 0.9 |
| Compound 51 | 1 |
| Compound 52 | 0.2 |
| Compound 55 | 0.1 |

It is apparent from the results shown above that the compounds of the present invention have an effect of inhibiting the activation of AP-1 and NF-kappa B, and they are useful for the treatment of inflammatory diseases caused through the transcription factors. Namely, they inhibit gene expression of inflammatory cytokines and matrix metalloprotease and inflammatory cell adhesion molecules. They can be used as anti-inflammatory agent, antirheumatic agent, immunosuppressant, cancer metastasis inhibitor, remedy for arteriosclerosis and antiviral agent which are free from hormonal side effects unlike steroids.

What is claimed is:

1. A benzene compound of formula (I) or a pharmaceutically acceptable salt thereof:

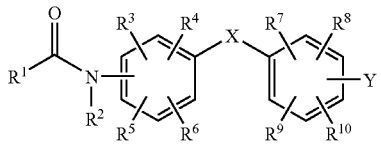

wherein $R^1$ represents a cycloalkyl group substituted with at least one substituent selected from the group consisting of a halogen atom, an alkyl group, an alkoxycarbonyl group, a cyano group, an amino group, an alkylamino group, and a protected amino group; or a cycloalkenyl group substituted with at least one substituent selected from the group consisting of a halogen atom, an alkyl group, an alkoxycarbonyl group, a cyano group, an amino group, an alkylamino group, and a protected amino group;

$R^2$ represents hydrogen atom or an alkyl group;

$R^3$ to $R^{10}$, which may be the same or different from each other, represent hydrogen atom, a halogen atom, hydroxyl group, mercapto group, nitro group, cyano group, trifluoromethyl group, an alkyl group, an alkoxyl group, an alkylthio group, an amino group which may be substituted with an alkyl group or an amino-protecting group, an acyloxy group, an acyl group, carboxyl group, an alkoxycarbonyl group or carbamoyl group;

—Y represents a group of formula (II):

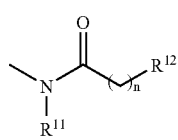

wherein $R^{11}$ represents hydrogen atom or an alkyl group; and $R^{12}$ represents:

an alkyl group which may have a substituent;

a cycloalkyl group which may be substituted with at least one substituent selected from the group consisting of a halogen atom, an alkyl group, an alkoxycarbonyl group, a cyano group, an amino group, an alkylamino group, and a protected amino group, wherein said cycloalkyl group is one member selected from the group consisting of a cyclopropyl group, a cyclobutyl group, and a cyclopentyl group;

a cycloalkenyl group which may be substituted with at least one substituent selected from the group consisting of a halogen atom, an alkyl group, an alkoxycarbonyl group, a cyano group, an amino group, an alkylamino group, and a protected amino group;

an aryl group which may have a substituent;

an aromatic heterocyclic group having one or more hetero atoms, which may have a substituent; or a saturated heterocyclic group having one or more hetero atoms, which may have a substituent;

n represents an integer selected from among 0 to 6; and

—X— represents an interatomic bond, or any of —O—, —O—CHR$^{17}$—, —CHR$^{18}$—O—, —O—CO—, —CO—O—, —O—CS—, —CS—O—, —S—, —SO—, —SO$_2$—, —S—CHR$^{19}$—, —CHR$^{20}$—S—, —S—CO—, —CO—S—, —S—CS—, —CS—S—, —SO$_2$—NR$^{21}$—, —NR$^{22}$—SO$_2$—, —NR$^{23}$—, —NR$^{24}$—CHR$^{25}$—, —CHR$^{26}$—NR$^{27}$—, —CO—, —C(=NOR$^{28}$)—, —C(=CHR$^{29}$)—, —CO—CHR$^{30}$—, —CHR$^{31}$—CO—, —CO—NR$^{32}$—, —NR$^{33}$—CO—, —CR$^{34}$R$^{35}$—, —CHR$^{36}$—CHR$^{37}$—, and —CR$^{38}$=CR$^{39}$— wherein $R^{17}$, $R^{18}$, $R^{19}$, $R^{20}$, $R^{21}$, $R^{22}$, $R^{25}$, $R^{26}$, $R^{29}$, $R^{30}$, $R^{31}$, $R^{32}$, $R^{33}$, $R^{34}$, $R^{38}$, and $R^{39}$ each represent hydrogen atom or an alkyl group, $R^{23}$, $R^{24}$, $R^{27}$ and $R^{28}$ each represent hydrogen atom, an alkyl group or an acyl group, $R^{36}$ and $R^{37}$ each represent hydrogen atom, hydroxyl group or an alkyl group, and $R^{35}$ represents hydrogen atom, hydroxyl group, mercapto group, cyano group, an alkyl group which may have a substituent, an alkoxyl group, an alkylthio group, an acyloxy group, an amino group which may be substituted with an alkyl group or an amino-protecting group, carboxyl group, an alkoxycarbonyl group or carbamoyl group.

2. The benzene compound or pharmaceutically acceptable salt of claim 1, wherein $R^1$ in formula (I) is a cycloalkyl group substituted with at least one substituent selected from the group consisting of a halogen atom, an alkyl group, an alkoxycarbonyl group, a cyano group, an amino group, an alkylamino group, and a protected amino group.

3. The benzene compound or pharmaceutically acceptable salt of claim 1, wherein $R^1$ in formula (I) is cyclopropyl group substituted with at least one substituent selected from the group consisting of a halogen atom, an alkyl group, an alkoxycarbonyl group, a cyano group, an amino group, an alkylamino group, and a protected amino group.

4. The benzene compound or pharmaceutically acceptable salt of claim 1, wherein $R^1$ in formula (I) is 2,2-dimethylcyclopropyl group or 2,2-dichlorocyclopropyl group.

5. The benzene compound or pharmaceutically acceptable salt of claim 4, wherein $R^{12}$ of formula (II) in formula (I) is 2,2-dimethylcyclopropyl group or 2,2-dichlorocyclopropyl group and n is 0.

6. The benzene compound or pharmaceutically acceptable salt of claim 1, wherein $R^3$ to $R^{10}$ in formula (I) are each hydrogen atom.

7. The benzene compound or pharmaceutically acceptable salt of claim 3, wherein $R^1$ in formula (I) is a cyclopropyl group substituted with at least one substituent selected from the group consisting of a halogen atom, an alkyl group, an alkoxycarbonyl group, a cyano group, an amino group, an alkylamino group, and a protected amino group, and the carbon atom on the cyclopropyl group adjacent to the carbonyl group has an absolute configuration S.

8. The benzene compound or pharmaceutically acceptable salt of claim 3, wherein $R^1$ in formula (I) is a cyclopropyl group substituted with at least one substituent selected from the group consisting of a halogen atom, an alkyl group, an alkoxycarbonyl group, a cyano group, an amino group, an alkylamino group, and a protected amino group, and the carbon atom on the cyclopropyl group adjacent to the carbonyl group has an absolute configuration R.

9. The benzene compound or pharmaceutically acceptable salt of claim 1, which is represented by formula (Ia):

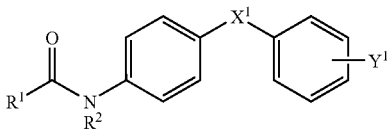

(Ia)

wherein $R^1$ and $R^2$ are as defined in formula (I);
$Y^1$ represents a group of formula (II);
$R^{12}$ represents:
an alkyl group which may have a substituent;
a cycloalkyl group which may be substituted with at least one substituent selected from the group consisting of a halogen atom, an alkyl group, an alkoxycarbonyl group, a cyano group, an amino group, an alkylamino group, and a protected amino group, wherein said cycloalkyl group is one member selected from the group consisting of a cyclopropyl group, a cyclobutyl group, and a cyclopentyl group;
a cycloalkenyl group which may be substituted with at least one substituent selected from the group consisting of a halogen atom, an alkyl group, an alkoxycarbonyl group, a cyano group, an amino group, an alkylamino group, and a protected amino group;
an aryl group which may have a substituent; or
an aromatic heterocyclic group having one or more hetero atoms, which may have a substituent; and
—$X^1$— represents —O—, —O—$CHR^{17}$—, —$CHR^{18}$—O—, —O—CO—, —CO—O—, —O—CS—, —CS—O—, —S—, —SO—, —$SO_2$—, —S—$CHR^{19}$—, —$CHR^{20}$—S—, —S—CO—, —CO—S—, —S—CS—, —CS—S—, —$SO_2$—$NR^{21}$—, —$NR^{22}$—$SO_2$—, —$NR^{23}$—, —$NR^{24}$—$CHR^{25}$—, —$CHR^{26}$—$NR^{27}$—, —CO—, —C(=$NOR^{28}$)—, —C(=$CHR^{29}$)—, —CO—$CHR^{30}$—, —$CHR^{31}$—CO—, —CO—$NR^{32}$—, —$NR^{33}$—CO—, —$CR^{34}R^{35}$—, —$CHR^{36}$—$CHR^{37}$— or —$CR^{38}$=$CR^{39}$— wherein $R^{17}$ through $R^{39}$ are as defined in formula (I).

10. An AP-1 and NF-kappa B activation inhibitor which comprises a benzene compound or a pharmaceutically acceptable salt thereof according to claim 1 as an active ingredient.

11. An inflammatory cytokine production inhibitor, matrix metalloprotease production inhibitor or inflammatory cell adhesion factor appearance inhibitor which comprises a benzene compound or a pharmaceutically acceptable salt thereof according to claim 1 as an active ingredient.

12. An anti-inflammatory agent, antirheumatic agent, immunosuppressant, cancerous metastasis inhibitor, remedy for arteriosclerosis and antiviral agent which comprises a benzene compound or a pharmaceutically acceptable salt thereof according to claim 1 as an active ingredient.

13. A pharmaceutical composition, comprising a benzene compound or a pharmaceutically acceptable salt thereof according to claim 1 and a pharmaceutically acceptable carrier.

14. A pharmaceutical composition, comprising a benzene compound or a pharmaceutically acceptable salt thereof according to claim 2 and a pharmaceutically acceptable carrier.

15. A pharmaceutical composition, comprising a benzene compound or a pharmaceutically acceptable salt thereof according to claim 3 and a pharmaceutically acceptable carrier.

16. A pharmaceutical composition, comprising a benzene compound or a pharmaceutically acceptable salt thereof according to claim 4 and a pharmaceutically acceptable carrier.

17. A pharmaceutical composition, comprising a benzene compound or a pharmaceutically acceptable salt thereof according to claim 5 and a pharmaceutically acceptable carrier.

18. A pharmaceutical composition, comprising a benzene compound or a pharmaceutically acceptable salt thereof according to claim 6 and a pharmaceutically acceptable carrier.

19. A pharmaceutical composition, comprising a benzene compound or a pharmaceutically acceptable salt thereof according to claim 7 and a pharmaceutically acceptable carrier.

20. A pharmaceutical composition, comprising a benzene compound or a pharmaceutically acceptable salt thereof according to claim 8 and a pharmaceutically acceptable carrier.

21. A pharmaceutical composition, comprising a benzene compound or a pharmaceutically acceptable salt thereof according to claim 9 and a pharmaceutically acceptable carrier.

* * * * *